(12) United States Patent
LaBarre et al.

(10) Patent No.: US 8,431,387 B2
(45) Date of Patent: Apr. 30, 2013

(54) CHEMICAL TEMPERATURE CONTROL

(75) Inventors: Paul Donald LaBarre, Suquamish, WA (US); Jay Lewis Gerlach, Kenmore, WA (US); Bernhard Hans Weigl, Seattle, WA (US); Gonzalo Jose Domingo-Villegas, Seattle, WA (US)

(73) Assignee: Program for Appropriate Technology In Health, Seattle, WA (US)

( * ) Notice: Subject to any disclaimer, the term of this patent is extended or adjusted under 35 U.S.C. 154(b) by 592 days.

(21) Appl. No.: 12/134,965

(22) Filed: Jun. 6, 2008

(65) Prior Publication Data
US 2009/0004732 A1 Jan. 1, 2009

Related U.S. Application Data

(60) Provisional application No. 60/942,383, filed on Jun. 6, 2007.

(51) Int. Cl.
*C12M 3/00* (2006.01)
*C12M 1/34* (2006.01)
*C12M 1/00* (2006.01)
*B06B 1/00* (2006.01)
*A61F 7/00* (2006.01)
*A61F 7/08* (2006.01)
*F24J 1/00* (2006.01)
*F24J 3/00* (2006.01)

(52) U.S. Cl.
USPC ............. 435/287.2; 126/204; 126/263.01; 126/263.03; 422/128; 435/283.1; 435/287.1

(58) Field of Classification Search .... 435/283.1–309.4; 126/263.01, 104, 204, 263.03; 422/138
See application file for complete search history.

(56) References Cited

U.S. PATENT DOCUMENTS

| | | | |
|---|---|---|---|
| 3,903,011 | A | 9/1975 | Donnelly |
| 3,976,049 | A | 8/1976 | Yamashita et al. |

(Continued)

FOREIGN PATENT DOCUMENTS

| | | |
|---|---|---|
| CN | 20051010771.1 | 4/2007 |
| WO | WO 2004/108287 A1 | 12/2004 |

OTHER PUBLICATIONS

International Search Report for PCT/US 08/07124, mailed Jan. 29, 2009, 1 page.

(Continued)

*Primary Examiner* — Nathan Bowers
*Assistant Examiner* — Lydia Edwards
(74) *Attorney, Agent, or Firm* — Sterne, Kessler, Goldstein & Fox P.L.L.C.

(57) ABSTRACT

Exothermic and/or endothermic chemical reactions in combination with phase change materials can produce output temperature(s) within strict tolerances without requiring expensive and complicated external equipment to generate and maintain an output temperature. Similarly, an exothermic phase change material, which generates heat as a consequence of crystallizing a supercooled liquid, can generate heat at a constant temperature, without requiring expensive and complicated external equipment, as a consequence of the liquid form of the exothermic phase change material being in equilibrium with the solid form of the exothermic phase change material. Numerous biological and chemical processes and/or diagnostic devices require a constant temperature or temperatures for set periods of time. An example completely non-instrumented diagnostic platform based on nucleic acid amplification is described, which is particularly suited for use in developing countries that may not have access to expensive and complicated external equipment.

24 Claims, 32 Drawing Sheets

U.S. PATENT DOCUMENTS

| | | | |
|---|---|---|---|
| 3,977,202 A | | 8/1976 | Forusz et al. |
| 4,067,313 A | | 1/1978 | Donnelly |
| 4,249,592 A | | 2/1981 | Greene |
| 5,461,867 A | | 10/1995 | Scudder et al. |
| D371,513 S | | 7/1996 | Scudder et al. |
| 5,626,022 A | | 5/1997 | Scudder et al. |
| 5,641,681 A | * | 6/1997 | Carter ................................ 436/4 |
| 5,809,786 A | | 9/1998 | Scudder et al. |
| 5,879,378 A | * | 3/1999 | Usui ................................ 607/96 |
| 5,941,078 A | | 8/1999 | Scudder et al. |
| 5,979,164 A | | 11/1999 | Scudder et al. |
| 6,092,519 A | * | 7/2000 | Fish et al. ................. 126/263.01 |
| 6,178,753 B1 | | 1/2001 | Scudder et al. |
| 6,248,257 B1 | * | 6/2001 | Bell et al. ......................... 252/70 |
| 6,266,879 B1 | | 7/2001 | Scudder et al. |
| 6,351,953 B1 | | 3/2002 | Scudder et al. |
| 6,482,332 B1 | | 11/2002 | Malach |
| 6,586,233 B2 | | 7/2003 | Benett et al. |
| 6,640,801 B2 | * | 11/2003 | Sabin et al. ............... 126/263.01 |
| 7,004,161 B2 | | 2/2006 | Kolb |
| 2003/0180216 A1 | * | 9/2003 | TeGrotenhuis et al. ........ 423/659 |
| 2004/0138712 A1 | * | 7/2004 | Tamarkin et al. .................. 607/3 |
| 2005/0129582 A1 | * | 6/2005 | Breidford et al. ............. 422/100 |
| 2006/0051252 A1 | * | 3/2006 | Yuan et al. .................... 422/102 |
| 2006/0246493 A1 | * | 11/2006 | Jensen et al. ....................... 435/6 |
| 2007/0089261 A1 | * | 4/2007 | Hansen et al. .................... 15/320 |

OTHER PUBLICATIONS

Written Opinion of the International Searching Authority for PCT/US 08/07124, mailed Jan. 29, 2009, 7 pages.
SPRINGFUSOR® http://www.gomedical.com.au/products/springfusor.php, retrieved on Jun. 4, 2008.
Extended European Search Report for EP 08827207.5, mailed Aug. 4, 2011, European Patent Office, 6 pages.

* cited by examiner

CHEMICAL TEMPERATURE CONTROL

CROSS REFERENCE TO RELATED APPLICATIONS

This application claims the benefit of U.S. application Ser. No. 60/942,383, filed on Jun. 6, 2007, which is hereby incorporated by reference in its entirety.

STATEMENT REGARDING FEDERALLY-SPONSORED RESEARCH AND DEVELOPMENT

Statement under MPEP 310. The U.S. government has a paid-up license in this invention and the right in limited circumstances to require the patent owner to license others on reasonable terms as provided for by the terms of GPH-A-00-01-00005 awarded by USAID.

Part of the work performed during development of this invention utilized U.S. Government funds. The U.S. Government has certain rights in this invention.

BACKGROUND OF THE INVENTION

1. Field of the Invention

The present invention generally relates to diagnostic devices, more specifically to non-instrumented biochemical diagnostic devices.

2. Background Art

There are numerous chemical and biological processes and diagnostic methods that require precisely controlled temperature conditions. One prominent example is the polymerase chain reaction (PCR), which allows for the specific amplification of a deoxyribonucleic acid (DNA) sequence from undetectable, small copy numbers to greater, detectable copy numbers. The ability to amplify DNA to detectable levels has made PCR an essential tool for diagnostics.

PCR requires multiple repetitions of heat cycles typically ranging from 50° C. to 95° C. A 95° C. incubation of the reaction mixture ensures melting of double stranded DNA, a drop in temperature to 50° C. allows annealing of primer sequences to the target DNA sequences, and subsequent extension by DNA polymerase at approximately 72° C. For a typical diagnostic 100-300 bp amplicon using a DNA polymerase with a polymerization rate of 20-100 bp/sec, the major limiting step is the time required to heat and cool the reaction mixture fluid to temperature for each cycle. Presently, energetically and technologically expensive thermal cyclers are required for this process. However, such thermal cyclers are prohibitive for many applications such as remote surveillance studies and diagnostics in clinical settings with limited resources, for example, in developing countries. There is a need in the art, therefore, for a simple, non-instrumented means that can provide output temperatures within relatively precise tolerances without the assistance of other equipment.

There are several other approaches for amplifying nucleic acid signal. The more compelling of which are isothermal. In one such example: Nucleic acid sequenced based amplification (NASBA), nucleic acid signal amplification is performed by amplification of RNA using three enzymes reverse-transcriptase, RNase H and T7 RNA polymerase. Combined with the right primers these enzymes can amplify RNA signal under isothermal conditions. Other examples of isothermal nucleic acid signal amplification are (but not limited to): transcription mediated amplification (TMA), strand displacement amplification (SDA), loop-mediated isothermal amplification (LAMP), and helicase dependent amplification (HDA). For all these technologies there is a need in the art, therefore, for a simple, non-instrumented means that can provide output temperatures within relatively precise tolerances without the assistance of other equipment.

Another example of a biological process useful in the field of molecular diagnostics is reverse-transcription to generate complimentary DNA (cDNA) from RNA. The enzyme reverse-transcriptase generates cDNA from RNA by extension of a DNA primer which is annealed to RNA oligonuceoltides. This reaction is typically performed in vitro between 37° C. and 55° C. cDNA is more stable than RNA. A device that can maintain temperature between 37° C. and 55° C. for 30 minutes or more would facilitate generation of cDNA in clinical settings with limited resources as means to stabilize the RNA signal.

BRIEF SUMMARY OF THE INVENTION

In one embodiment, an assay platform comprises a heating element and a reaction vessel. The heating element comprises an exothermic chemical reagent mixture and a temperature regulating element comprising a phase change material that thermally cooperate to maintain a constant output temperature for a time duration.

In another embodiment an assay platform comprises a heating element and a reaction vessel. The heating element comprises an exothermic phase change material that generates heat as a consequence of crystallizing a supercooled liquid and generates heat at a constant temperature as a consequence of the liquid form of the exothermic phase change material being in equilibrium with the solid form of the exothermic phase change material.

In yet another embodiment, an assay platform comprises a first heating element, a second heating element, and a reaction vessel. The first and second heating elements comprise an exothermic chemical reagent mixture. The heating elements have defined working temperatures as well as defined working durations that are different from each other, resulting in an assay platform having multiple heating plateaus.

With such platforms, it is possible to perform, reverse-transcription, isothermal nucleic acid signal amplification and highly sensitive and specific PCR assays. Two exemplary embodiments of non-instrumented heat cyclers are disclosed. The first, Exothermal Circulation PCR, is based on the circulation of a liquid in an upright, closed-loop channel that is heated though exothermal heat pads to different temperature levels at different locations along the channel. The circulation is induced by the resulting differential in density of the liquid portions that are at higher and lower temperatures. The second variant, Linear Exothermal PCR, heat cycles a liquid that is wicked repeatedly through a channel over exothermal heat pads by the sample pad of a lateral flow strip (LFS) that detects the amplicons generated during the heat cyclings.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

Figure 23:
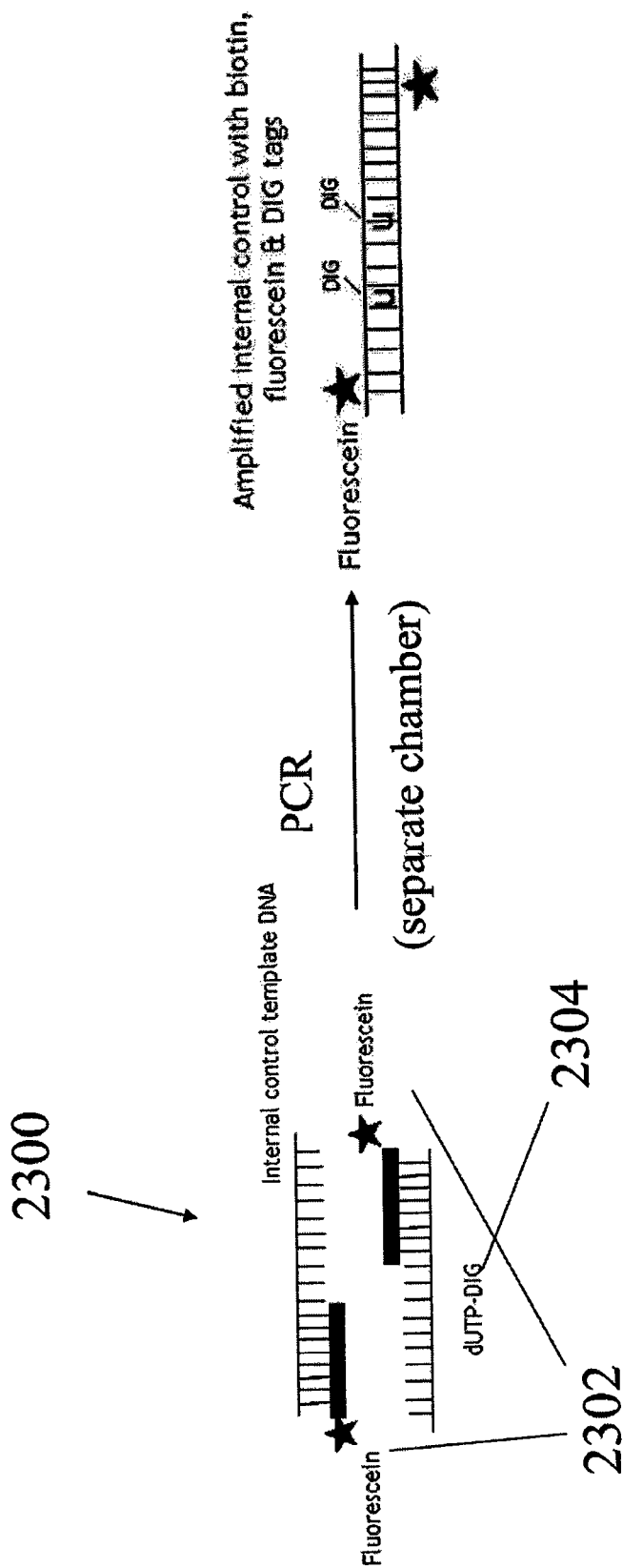
FIG. 23 is a schematic of an internal control DNA sequence being labeled by fluorescein tags and no biotin.
Figure 24:
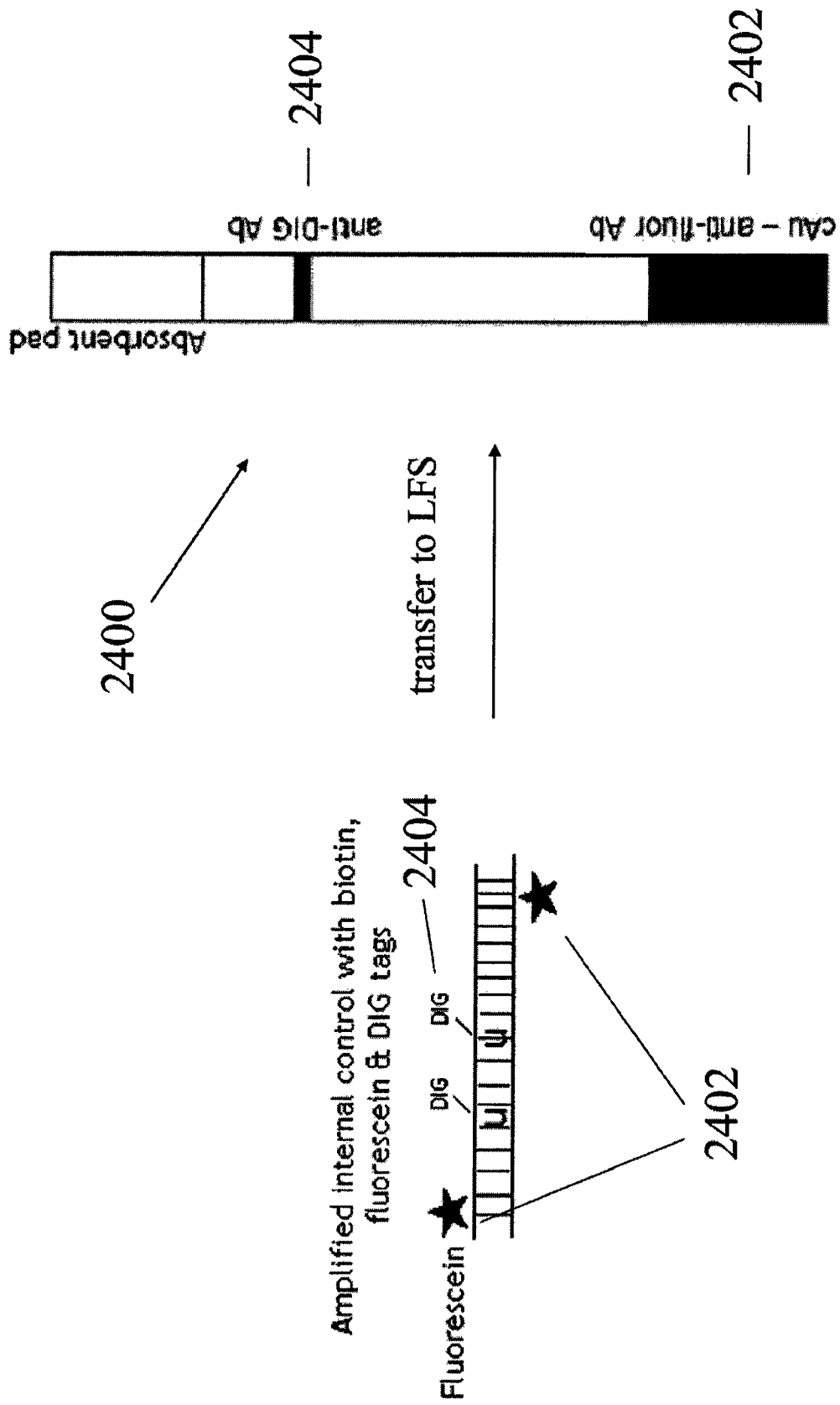
Figure 25:
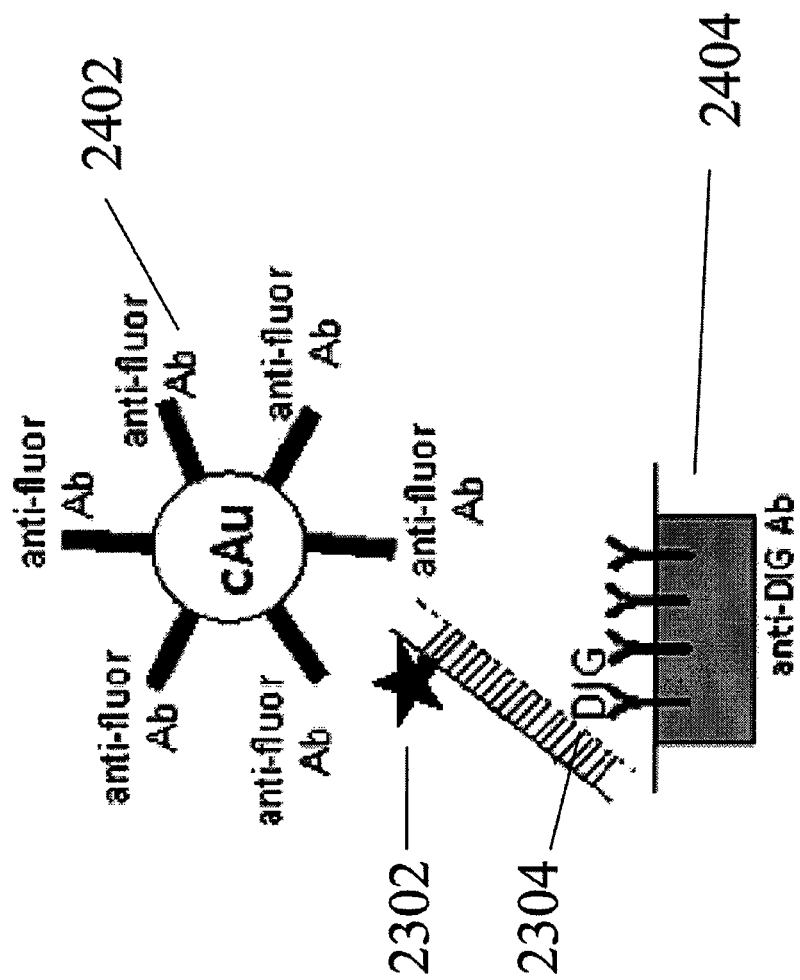
Figure 26A:
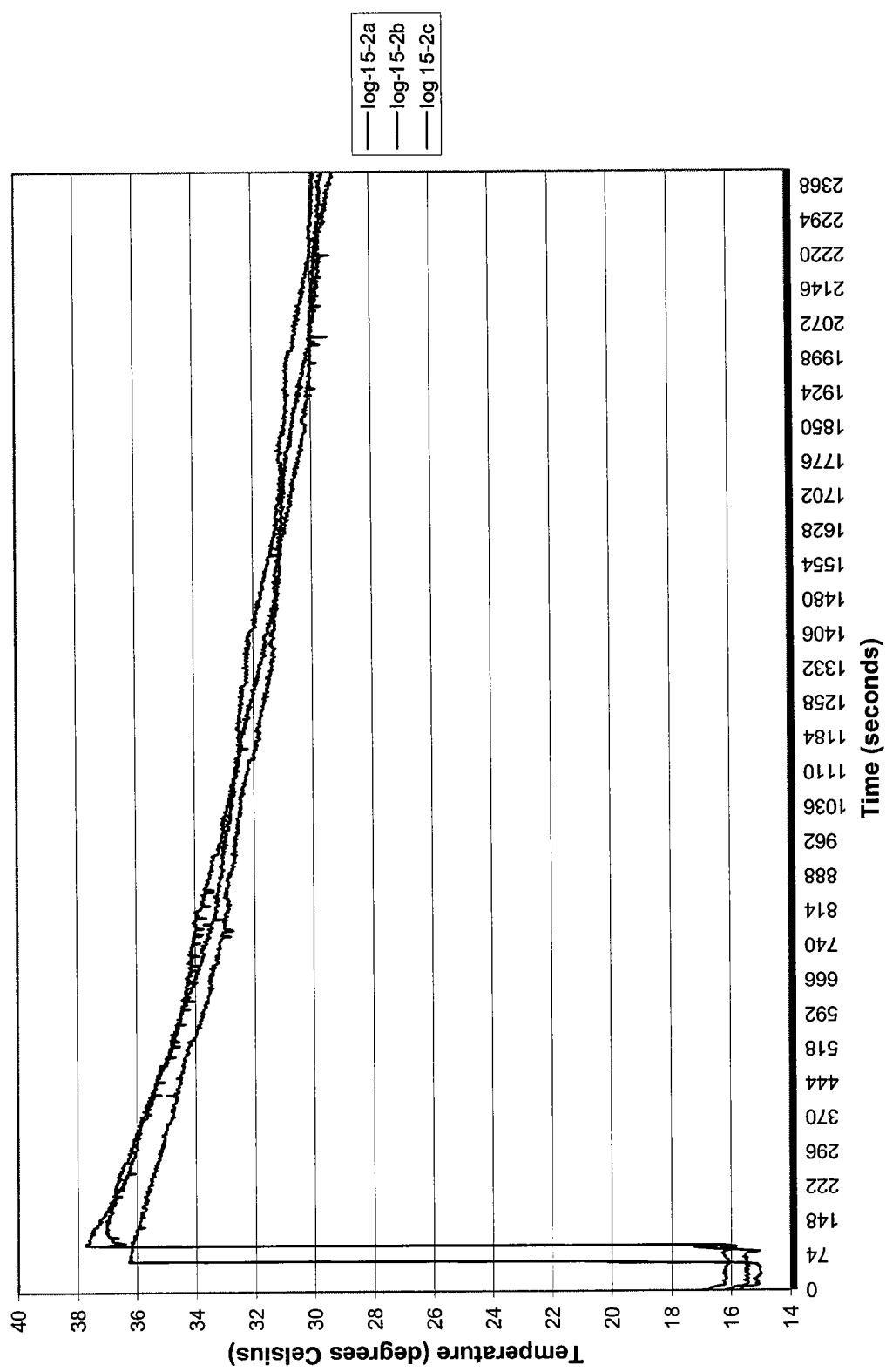
Figure 26B:
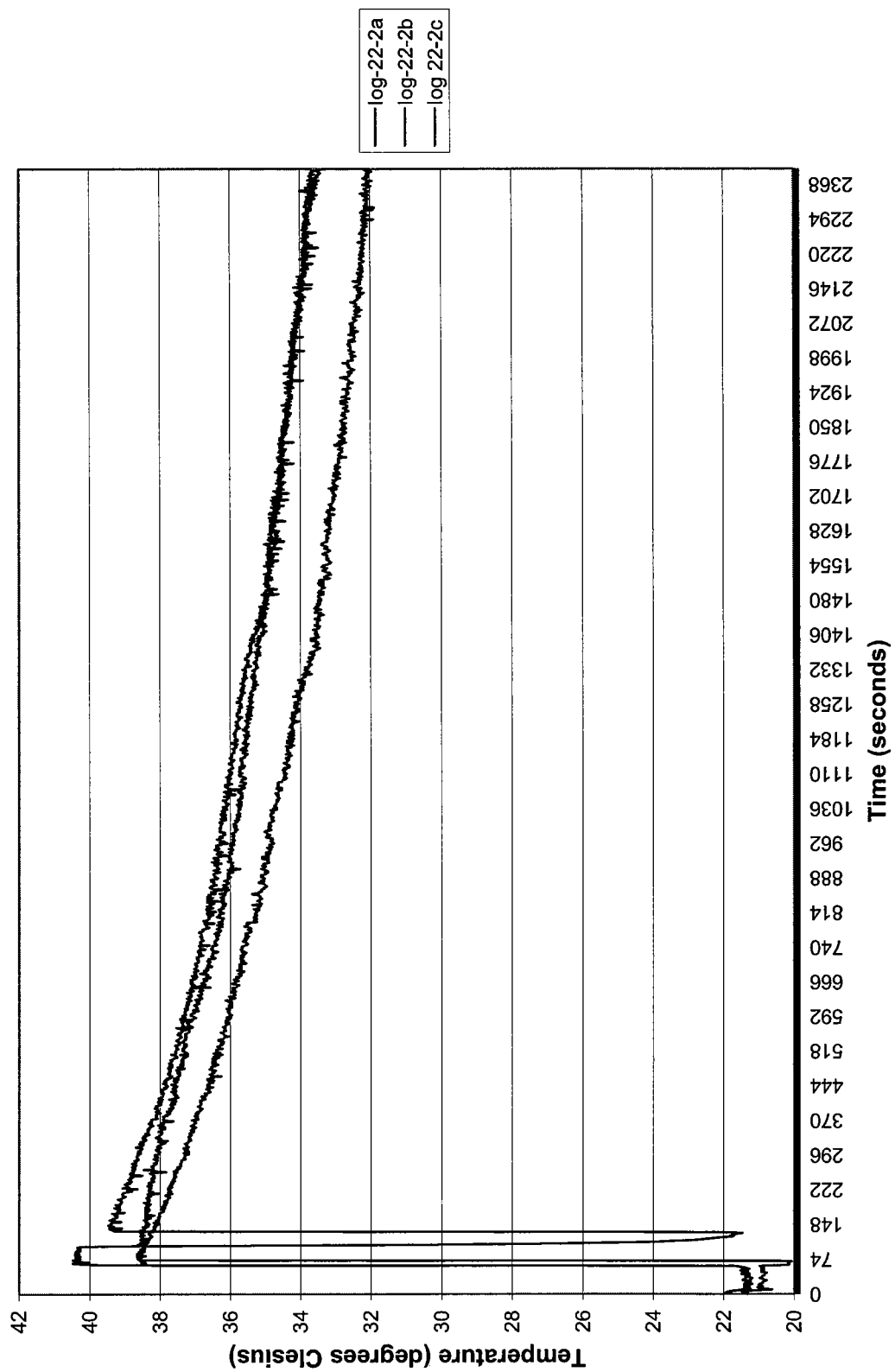
Figure 26C:
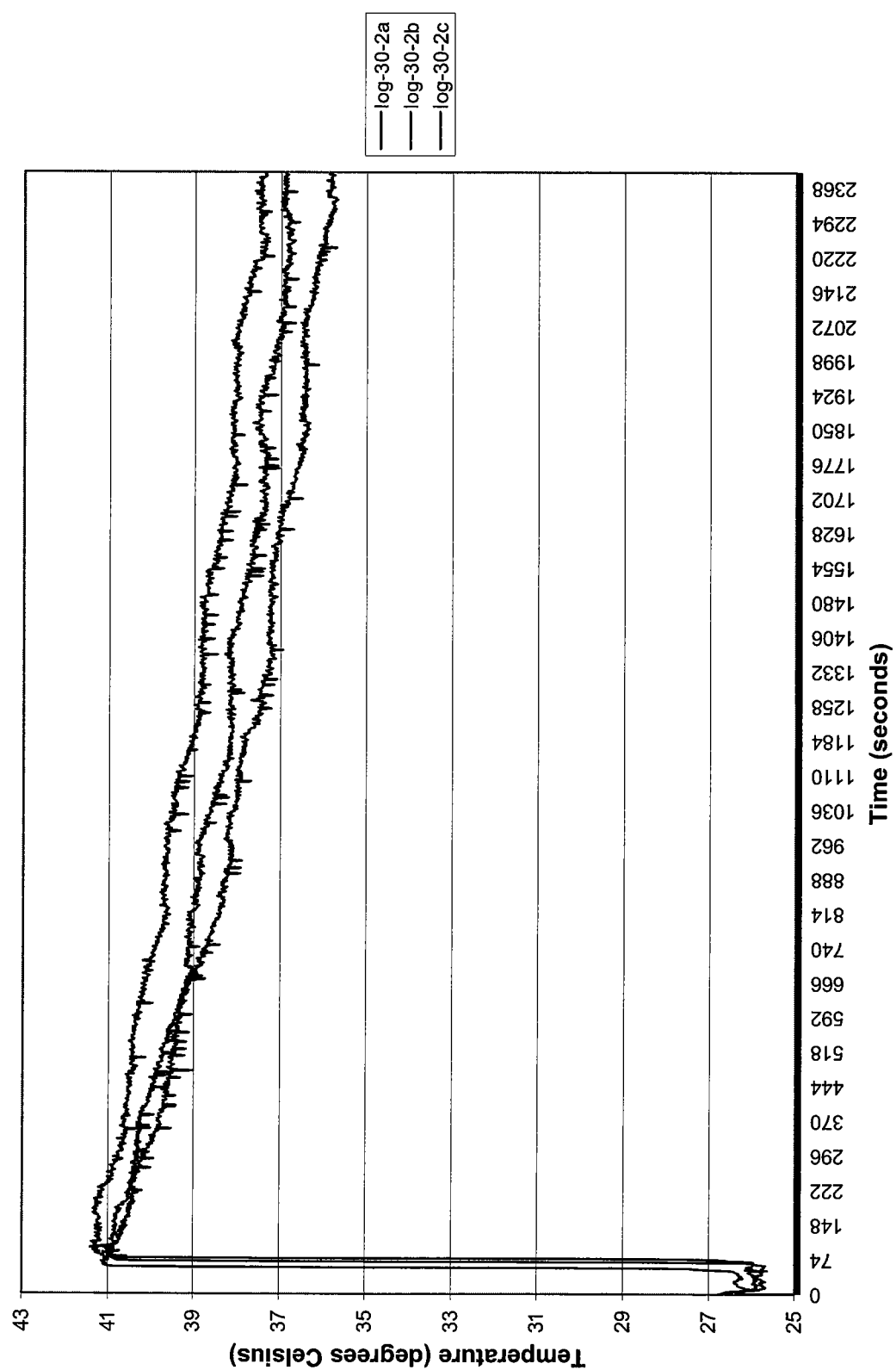
Figure 27A:
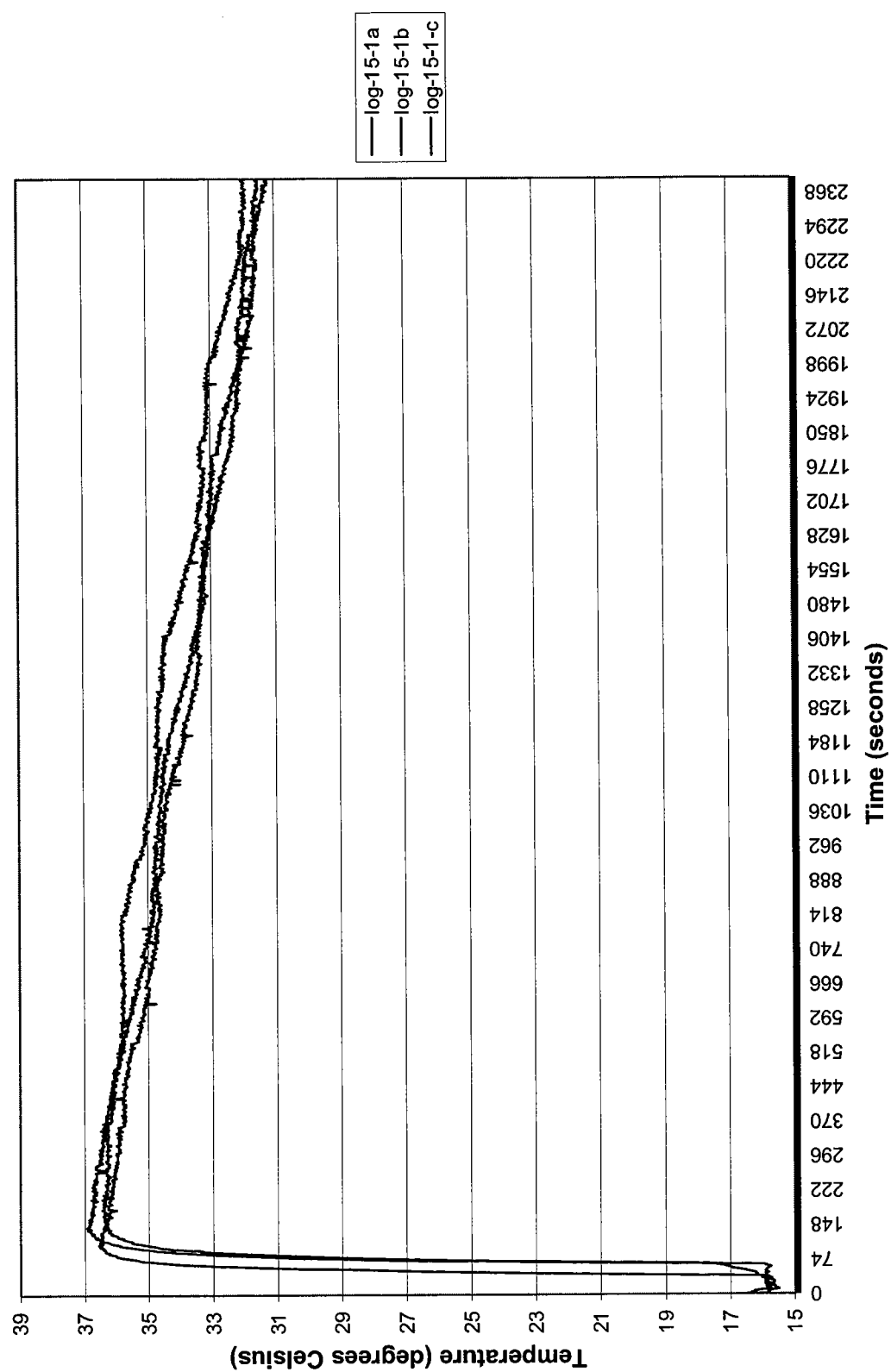
Figure 27B:
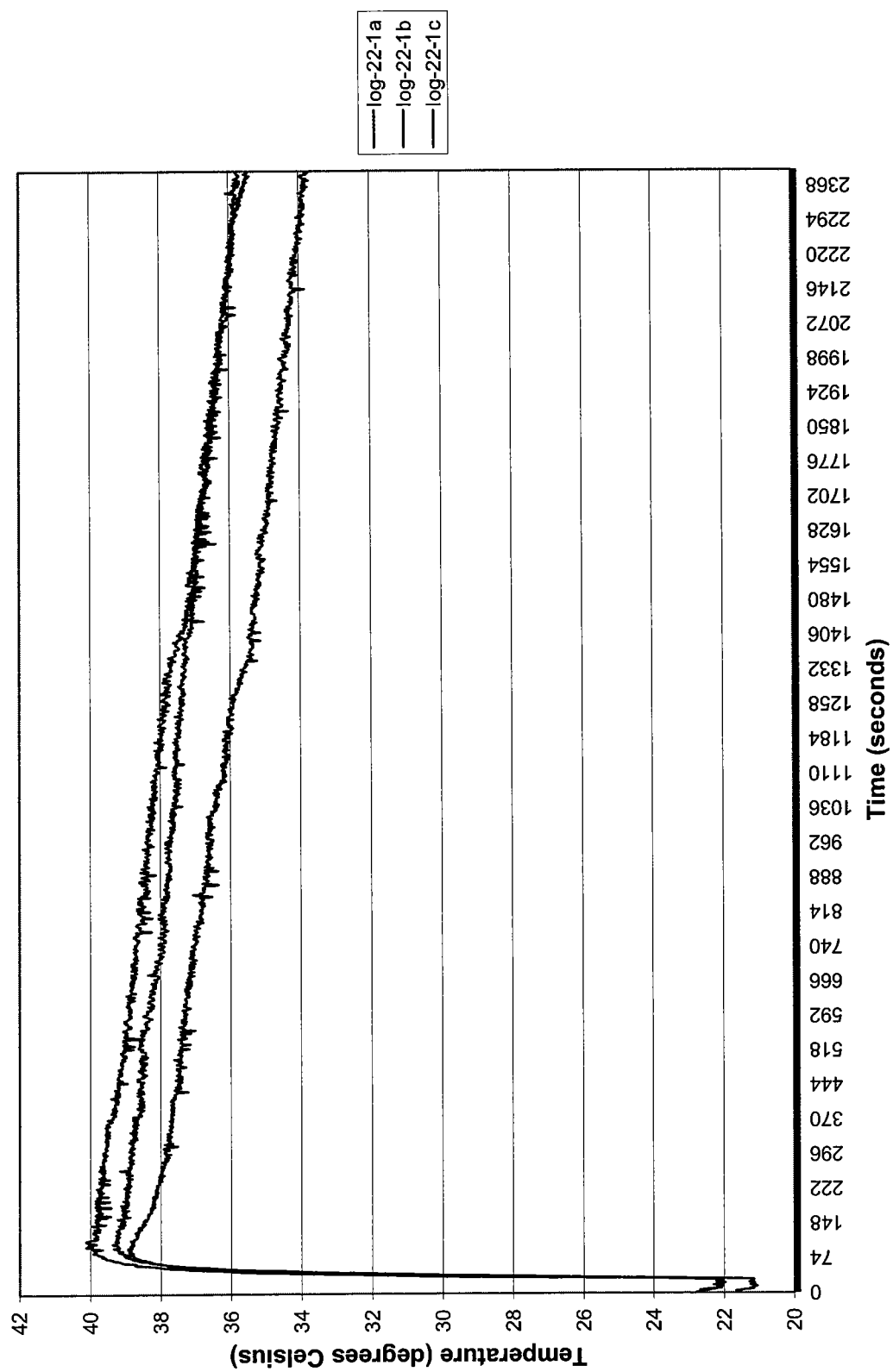
Figure 27C:
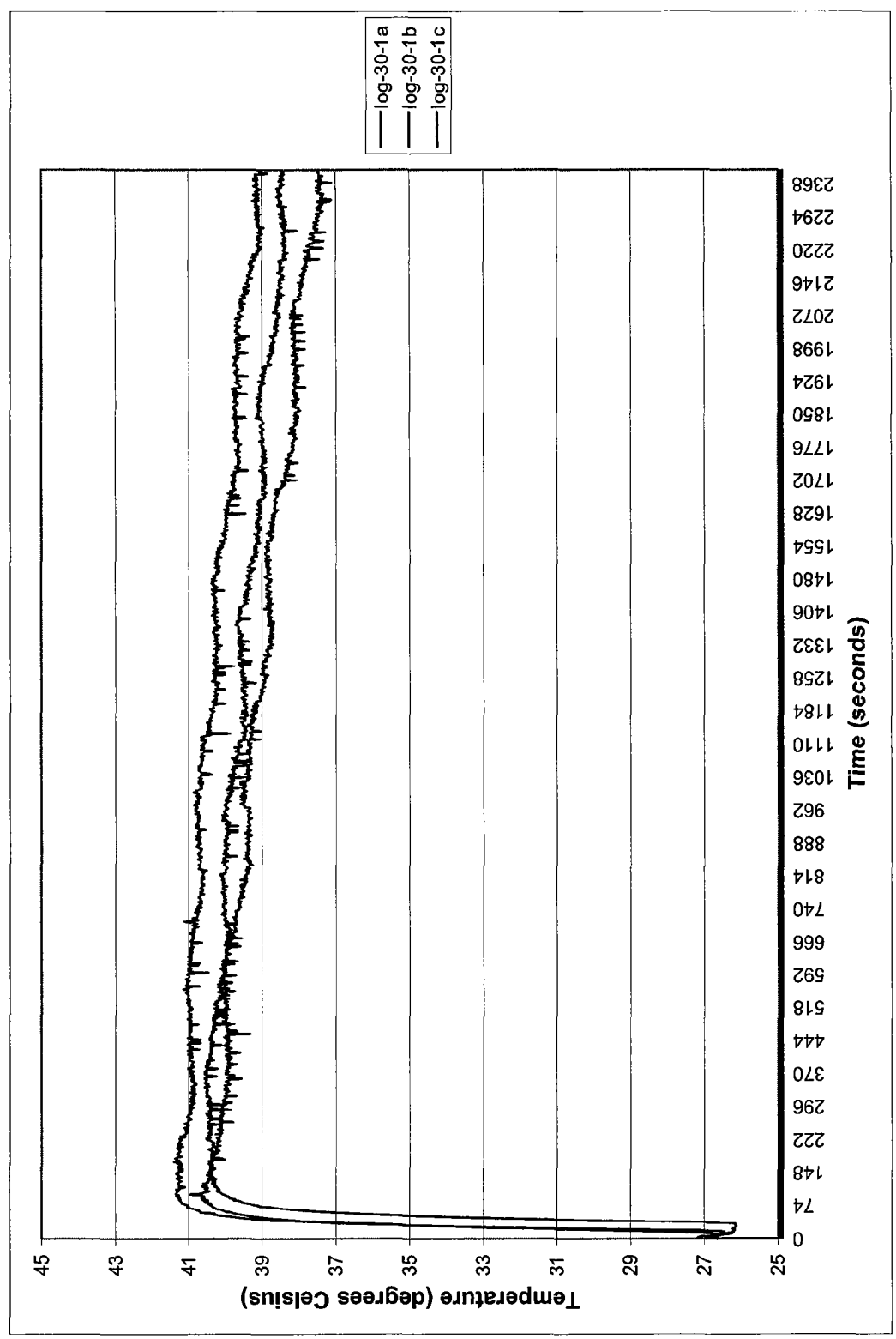
Figure 28:
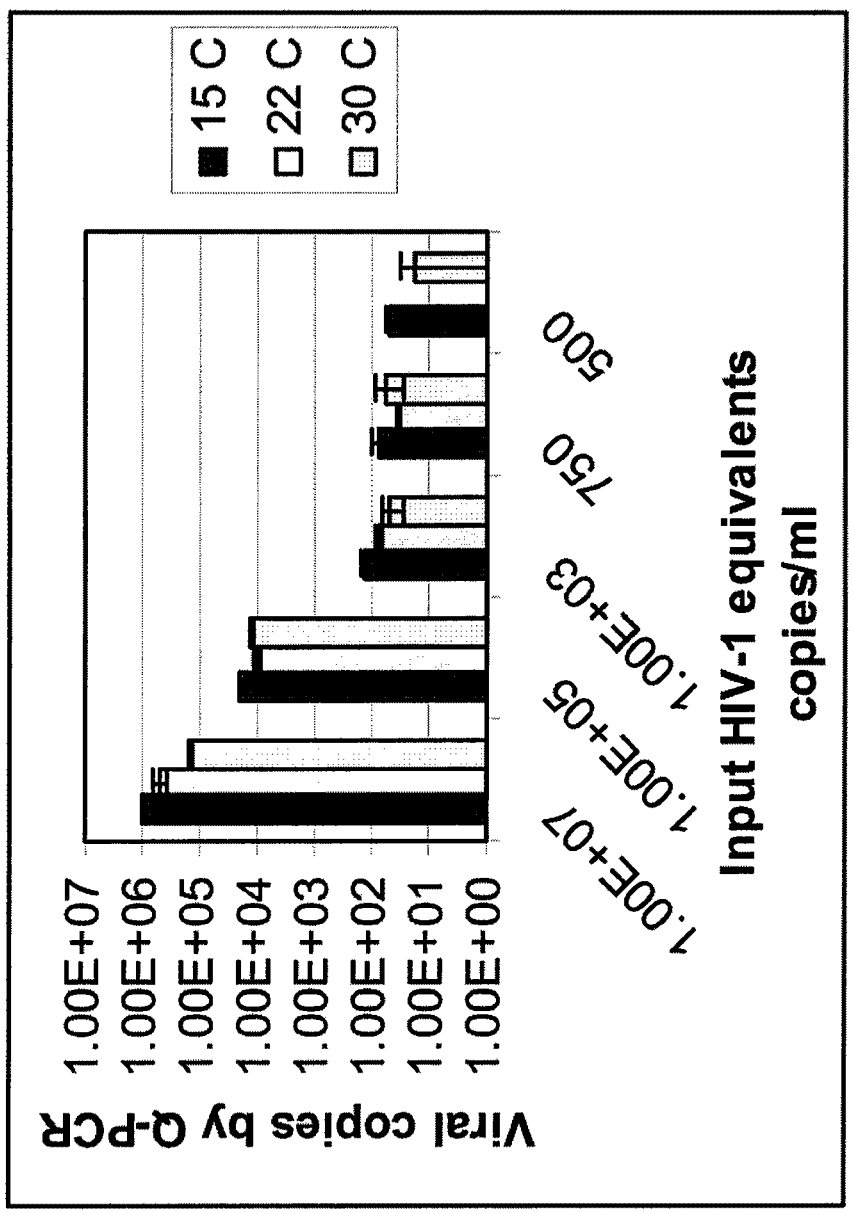

FIG. 24 a schematic of a second lateral flow strip used to detect the labeled DNA of FIG. 23;

FIG. 25 is a schematic depicting the binding of the DNA on the lateral flow strip of FIG. 24;

FIGS. 26 A-C are temperature profiles of a heat mixture in a reverse transcription (RT) reaction;

FIGS. 27 A-C are temperature profiles of an RT mixture in a reverse transcription reaction;

FIG. 28 is a graph comparing Q-PCR values for RT performed in the same temperature profiles as those generated by exothermic heat packs.

DETAILED DESCRIPTION OF THE INVENTION

The present invention is now described with reference to the figures where like reference numbers indicate identical or functionally similar elements. Also in the figures, the left most digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing form the spirit and scope of the invention.

A chemically engineered heating/cooling element according to the present invention can overcome the disadvantages of prior heating/cooling elements. Exothermic reactions are those that liberate heat, thereby increasing the temperature of the surroundings. Endothermic reactions require a heat input to proceed, thereby decreasing the temperature of the surroundings by absorbing heat from them. A phase change material will undergo an isothermal process as it either accepts or liberates latent heat from or to the surroundings. As long as the phase change material exists in multiple phases in equilibrium, its temperature will remain constant. A properly designed heating/cooling element can use exothermic or endothermic chemical reagent mixtures along with appropriate phase change materials to achieve a desired temperature output within the strict tolerances that biochemical processes require, eliminating the need for electrical energy input as well as expensive, bulky, and complicated feedback and control systems.

Chemical Heating and Chemical Cooling

The chemical processes disclosed herein, which provide heat/cooling are preferred to electrical means such as platinum film resistors or Peltier thermocouples because they do not require external energy sources. Additionally, such chemical reactions are capable of self-regulating temperature thereby eliminating the requirement for RTD temperature detection and proportional-integral-derivative (PID) controls. In addition to PCR and isothermal nucleic acid (NA) amplification applications, these chemical reactions are suitable for multiple other diagnostic applications, including, for example, the incubation phase of immunoassays. Chemical heating/cooling elements according to the present invention are particularly well-suited for microfluidic devices because the mass of the reagents can be very small. However, these chemical heating/cooling elements can replace conventional heating elements in many applications, as would be apparent to one or ordinary skill in the art in view of the following disclosure.

An exemplary chemical heating element comprises a mixture of iron, water, cellulose, vermiculite, activated carbon and salt. When the iron in the heating element is exposed to oxygen in the air, it oxidizes. In the process of doing so, heat is created. The salt acts as a catalyst and the carbon helps disperse the heat through the element. The vermiculite acts as an insulator, keeping the heat from dissipating too rapidly. Temperature regulation can be introduced into this system using thermally activated phase-change materials (waxes or polymers) encapsulated in carbohydrate spheres. The advantage of phase-change materials is that they can be customized to very specific temperatures. Temperature is regulated at the latent heat of absorption until all the material undergoes phase change.

Exothermic reactions for such purposes are typically activated by exposure to air humidity, oxygen, or by bringing two reaction components in close contact. Such mixtures can achieve temperatures ranging from slightly above body temperature to over to 100° C.

As an example, reactions and requirements particularly suited to PCR will now be discussed. Chemical heat zones must be designed such that specific heat zone passes are adequate to ensure DNA amplification but also of sufficiently short duration to ensure the total test time is less than 15 minutes. In order to be economically attractive, battery powered heating must be avoided. There are several criteria that this particular application demands of the reactions. First, the reaction must release an amount of heat sufficient to heat the zone of fluid up to the melting temperature of DNA (about 90-95° C.). Secondly, the reaction must last long enough for the reactants to cycle through the thermal loop a sufficient number of times. This imposes a minimum heat evolution time of approximately 10 minutes. Third, the heat evolved in the reaction must keep the heat zone within a narrow temperature range for the PCR to work. The two temperatures which are necessary are the melting temperature (about 90-95° C.), and the annealing temperature (about 45-55° C.). The reaction should not deviate from these temperatures by more than about 5 degrees, preferably not more than 1 or 2 degrees. And finally, the reactants that compose this reaction must be relatively safe and durable. Diagnostic cards which incorporate chemical reactions may undergo elevated temperatures when transported, and could be handled by relatively inexperienced operators, so a malfunction of the reaction or spilling of the reactants should not result in a serious or fatal injury. Optimal chemical mixtures should be selected to establish and maintain stable temperature zones through the PCR cycles. Additionally, the size and shape of the temperature zones (discussed later) as well as the reaction channel geometry (discussed later) will largely depend on the optimal PCR cycle times through each zone. Several suitable exothermic reactions will now be described.

Figure 1:
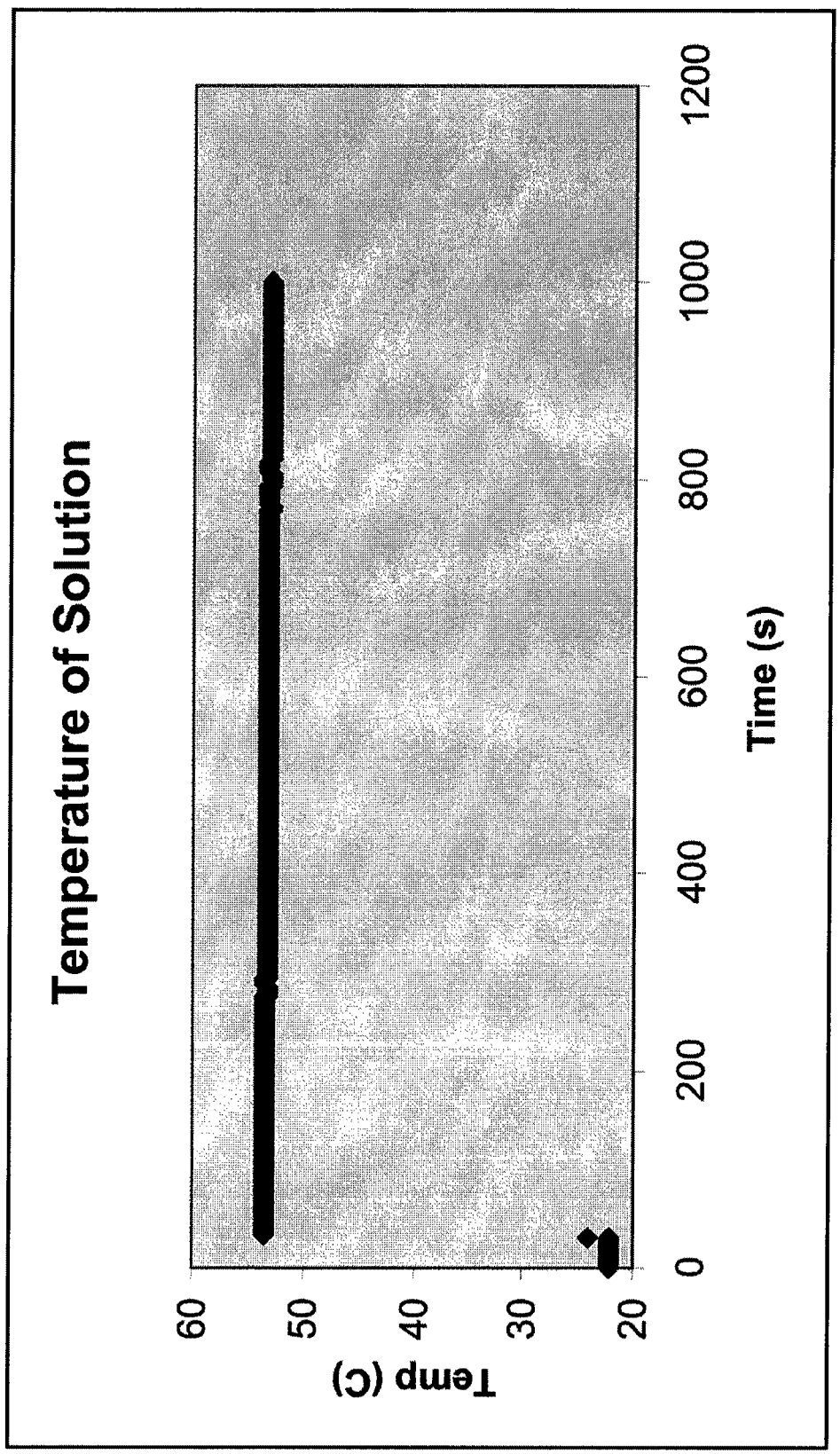
FIG. 1 is temperature profile of an acetate crystallization reaction.

The triggering or sudden nucleation of a supercooled solution is an exothermic reaction. One example of such a reaction, acetate crystallization, $CH_3COONa_{(l)} \rightarrow CH_3COONa_{(s)}$, is a simple phase change reaction. For example, a flask of water, supersaturated with sodium acetate at an elevated temperature (e.g., 73.1 g per 50 ml of water at 70° C.), and then allowed to cool to room temperature (which usually takes approximately 3 hours), is relatively stable if kept pure, but if it is seeded with a small crystal of sodium acetate, activated via mechanical friction or shock (for example with a metal clicker), exposed to an electrical current, or even if dust is allowed to settle on it, it will begin to crystallize. In general, a supercooled solution can be triggered to crystallize by seeding it with the same anhydrous or hydrated crystals, mechanical friction or shock (e.g., metal clicker, metallic snap disc, sharp needles, shaking, etc.), exposure to electrical currents, etc. This reaction emits a considerable amount of heat (approximately 250 J/g), and when it begins to fuse, the mixture will almost instantly jump to 54° C. (as shown at 100 of FIG. 1), the melting point of sodium acetate. The crystallization of other supercooled substances may produce different temperatures. On the other hand, if kept sealed, the mixture is quite stable; it can be poured, moved around, etc. This reaction can be used, for example, to regulate the cooling (annealing) portion of the PCR loop. Since this reaction is itself a phase change reaction, the temperature remains constant without the need to add a separate phase change material, e.g., a paraffin. Accordingly, a heating element may comprise a material that acts both as an exothermic heating element and as a temperature regulating element to heat and regulate the temperature of a reaction vessel. One example of such a heating element is a supersaturated salt solution, such as a supersaturated sodium acetate solution, that generates heat as it transitions from a liquid state to a solid state. As such, such a material is referred to herein as an exothermic chemical phase change material (ECPCM). Nevertheless, the effectiveness of the temperature control cab be augmented by adding an additional PCM to the ECPCM.

The introduction of initial crystal seeds of the same solute or other similar crystalline substances, the size of the seeds, the manner in which the seeds are added, and the processing or handling of the melt after the addition of the seeds are controllable factors which are effective in precipitating nucleation. Nucleation of supercooled liquid solutions can also be induced by surface energy in the form of dislocations and surface charge on a variety of materials (seeds) when they are in an active state. PCMs can be nucleated by adding sodium tetraborate decaydrate, sodium sulfite heptahydrate, or the like. The temperature produced by the crystallization reaction can be controlled by, for example, adding another material to the supercooled liquid solution to form a mixture. For example, when ethylene glycol is added to some PCMs, the temperature produced at crystallization decreases in accordance with the amount of ethylene glycol added.

Figure 2:
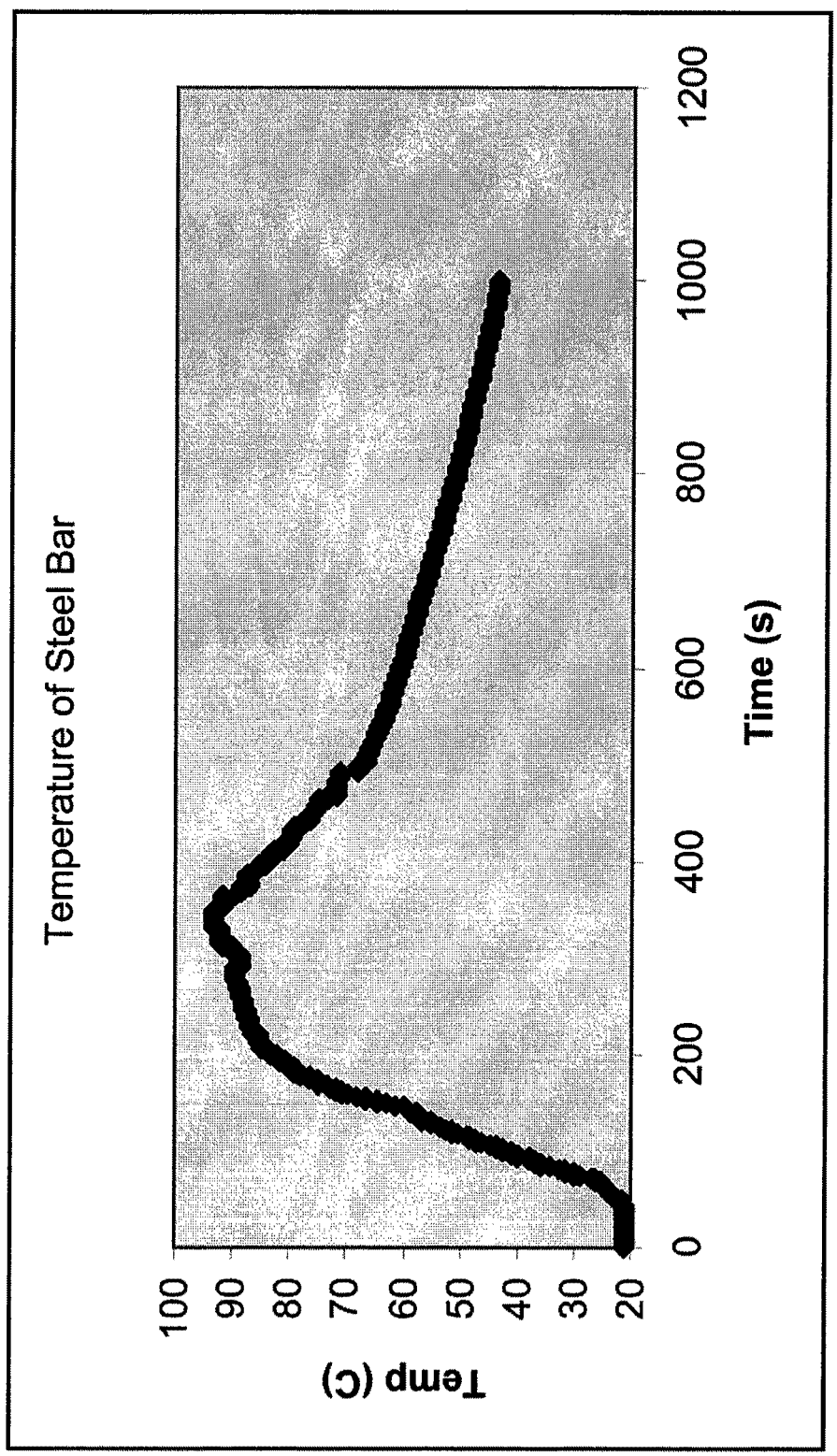
FIG. 2 is a temperature profile of a reduction reaction of copper with Magnesium.

Unlike ECPCMs, exothermic chemical reagent mixtures (ECRMs) are not simple phase change reactions. For example, the reduction of Copper with Magnesium, $Mg_{(s)}+CuSO_{(s)}MgSO_{(s)}+Cu_{(s)}$ (as shown in FIG. 2), is a basic redox reaction. Dry magnesium powder is mixed with dry cupric sulfate in an equal molar ratio. This mixture is relatively stable until a medium for conduction, such as water, is added. At this point, the reaction violently commences, forming solid copper. Water must be continuously added to this solution; it will not proceed on its own. It is an extremely potent reaction (2844 J/g), which explains the fast temperature rise shown at 200 in FIG. 2. Furthermore, the heat of the reaction makes the water boil, thus limiting the maximum temperature of the reaction to 100° C., which is very close to a desired temperature in the heating (denaturing) sector of the PCR loop. In the experiment shown in FIG. 2, the temperature stays at 92±2° C. for almost a full minute. This time can be extended by using more reactant (the experiment of FIG. 2 was done using less than a gram of total reactant).

Figure 3:
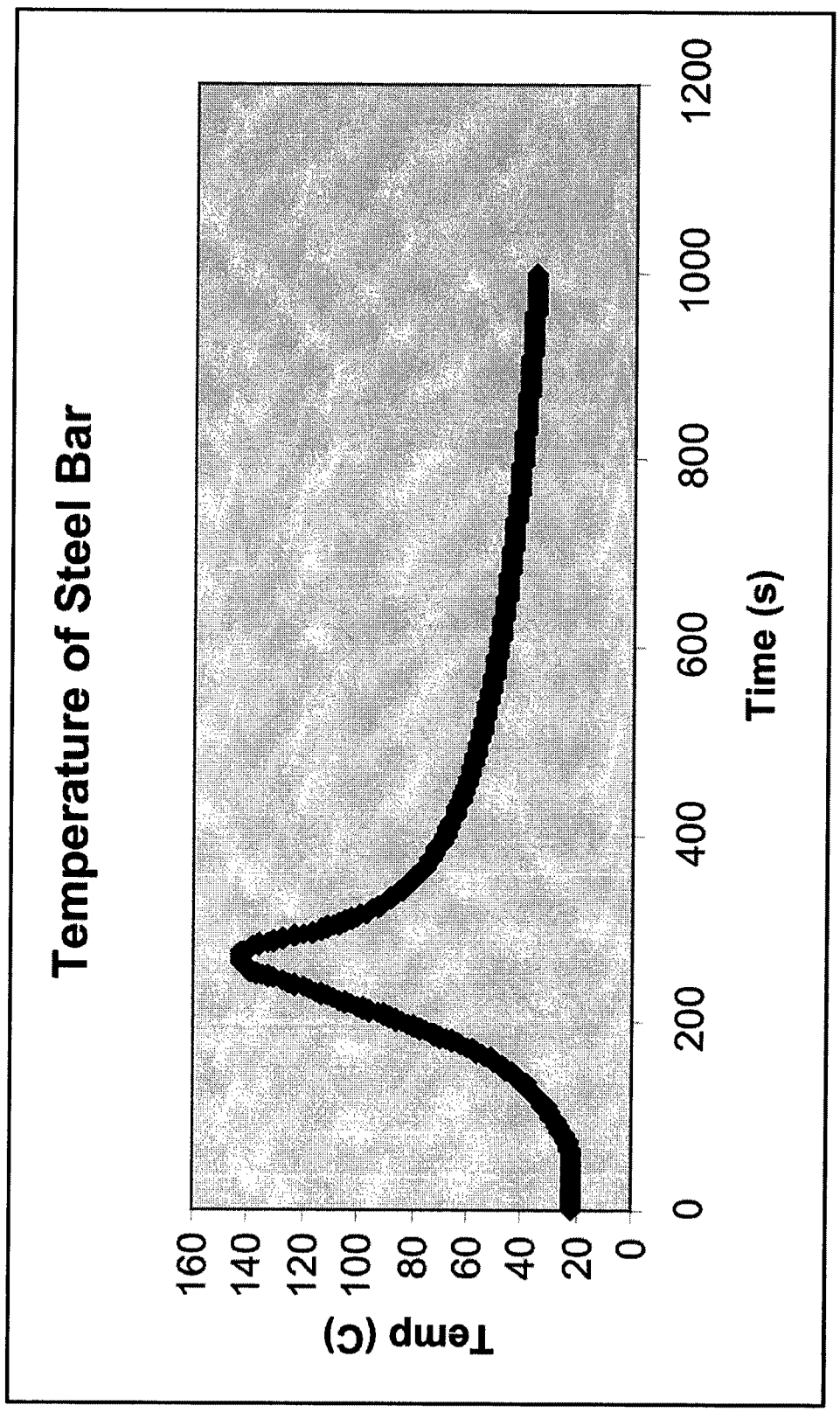
FIG. 3 is a temperature profile of a calcium oxide hydration reaction.

Another ECRM reaction is calcium oxide hydration, $CaO+2\ HCl+H_2O \rightarrow CaCl_2 \cdot 2\ H_2O$. The factor that makes it attractive in this particular application is how readily it absorbs water, and how exothermic this particular reaction is. As a demonstration, a small mass of calcium oxide (approximately 1.5 g) may be mixed with 5-10% trehalose and packed into a tablet using a hand press and a mold. This tablet may then be packed into a reaction well designed to reveal the potential of this reaction by measuring the temperature of a small steel rod in the bottom of the well using a thermocouple. 1 M HCl is added to the top of this tablet at a rate of ~20 µl per 4 seconds using a pipetman. The resulting temperature measurements are shown in FIG. 3. It is clear from this figure that a small amount of quicklime was able to heat the steel rod up to temperatures exceeding 140° C. (see 300 in FIG. 3). Furthermore, this reaction is very simple to conduct. The water from the top of the tablet has no problem diffusing past the top layers of the calcium oxide, so that in order to keep the reaction going, one must merely keep delivering water. The only complication is that the calcium oxide expands substantially when undergoing this reaction, and this must be accounted for in the design. In addition, its large exothermic release must be regulated to keep a constant temperature (e.g. 55° C., 74° C., 94° C., or combinations thereof).

Another ECRM reaction is the formation of rust: $4\ Fe+3\ O_2+H_2O \rightarrow 2\ Fe_2O_3 \cdot H_2O$. This can generate high temperatures for an extended period of time, but it requires a fairly extensive balance of chemicals.

The basic neutralization reaction, $H_3O^+ + OH^- \rightarrow 2\ H_2O$ is also an ECRM. The potential energy for this reaction is rooted in manipulating the concentrations of acid and base, and can generate a large amount of heat.

The ECRM reaction $Mg+2\ HCl \rightarrow MgCl_2+H_2$ generates considerable heat, but also emits a considerable amount of flammable hydrogen gas. This can be circumvented with the use of a hydrogen chelator or sponge, but this inevitably raises the complexity, and thus cost, of the device.

Embodiments could also comprise chemical cooling zones, incorporating endothermic chemical reactions. For example, chemical cooling can be used to keep drugs, vaccines, or biological materials at a certain temperature. U.S. Pat. No. 3,977,202, incorporated herein by reference, gives a recipe comprising a mixture of sodium acetate trihydrate and ethylene glycol that can hold a temperature of 14° F. for close to 3 hours in a sealed jar at room temperature.

Uses of Phase Change Material

In some applications, the temperature of a heat zone (or cool zone) must be restricted to maintain a narrow band. For this purpose, a barrier is inserted between the reaction and the zone. This barrier may be composed of a phase change material (PCM) (e.g., a paraffin, wax or polymer, salt hydrates, or non-paraffin organics) that melts (or freezes, boils, or condenses) at the desired temperature. One such example is Paraffin C21-C50 which has a melting temperature in the range 58° C.-60° C. Many different types of materials can act as PCMs, for example, metals, inorganic compounds, inorganic eutectics, organic compounds, and the like.

The reaction will heat the PCM, which in turn will heat the zone on the other side of the PCM. Once the melting temperature of the PCM is reached, the PCM will begin to melt. If a sufficient mass of PCM is used, an equilibrium between the liquid and solid phases of the PCM will exist as the PCM continues melting. This will keep the zone in contact with the PCM at the exact melting temperature for an extended period of time. The temperature of the PCM will begin to rise again once all of the PCM is melted, but if the amount of exothermic reactant is carefully managed, the reaction will end before all of the PCM is melted. As the PCM begins cooling, the solid and liquid phases of the PCM are still in equilibrium; therefore, the amount of time that the zone spends at the melting temperature of the PCM can be effectively doubled. If the zone is a cooling zone, the PCM material may be a liquid that starts to freeze after an endothermic chemical reaction proceeds; the PCM will keep the temperature constant as the PCM freezes. For PCM materials that are solids or liquids at ambient conditions, a "forward" phase change reaction is melting or vaporizing, respectively. The corresponding "reverse" phase change reactions are freezing and condensing.

Figure 4:
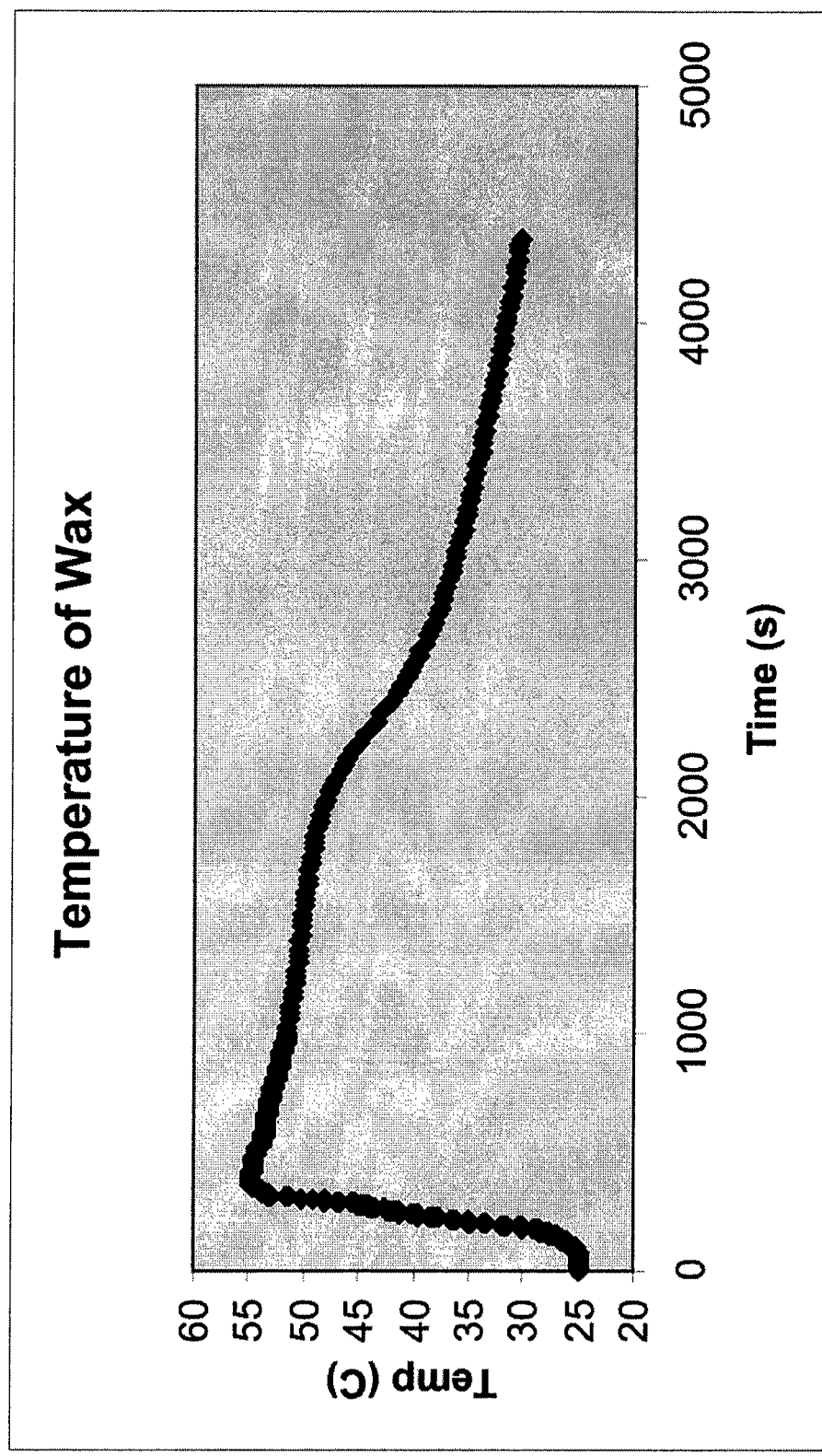
FIG. 4 is a temperature profile of a phase change reaction of wax.

Exemplary PCM materials are manufactured by Rubitherm Co. RT64 refers to a wax that is advertised to melt at 64° C. and RT100 refers to a wax that is advertised to melt at 100° C. As a demonstration, FIG. 4 was derived by use of a calorimeter. Approximately 10 mL of molten RT64 was poured into the phase change chamber of the calorimeter. The chamber was capped with a stainless steel plate, and 20 g of Calcium Oxide was loaded above it. 500 microliters of 1 N HCl was added every four seconds (distributed evenly across the top) to the CaO. Acid continued to be added until the CaO appeared completely saturated with aqueous solution. As shown in FIG. 4, a period of constant temperature (see 400 in FIG. 4) at the melting point. The wax stays at its melting point (51±2° C.) for approximately 18 minutes. As such, the CaO/RT64 mixture can regulate temperature to a value appropriate for the annealing section of a PCR cycle with a high degree of precision.

Chemical Thermal Cyclers

A customizable temperature profile can be generated by timing various endothermic and/or exothermic chemical reactions. Further, if PCM materials are incorporated the temperature profile can have one or more stable plateaus. In this way, a completely chemical thermal cycler can be devised which can replace expensive prior thermal cyclers. Such a thermal cycler would be advantageous for any application requiring one or more well-defined temperatures, such as in low-cost diagnostic devices intended for use in developing countries.

Figure 5:
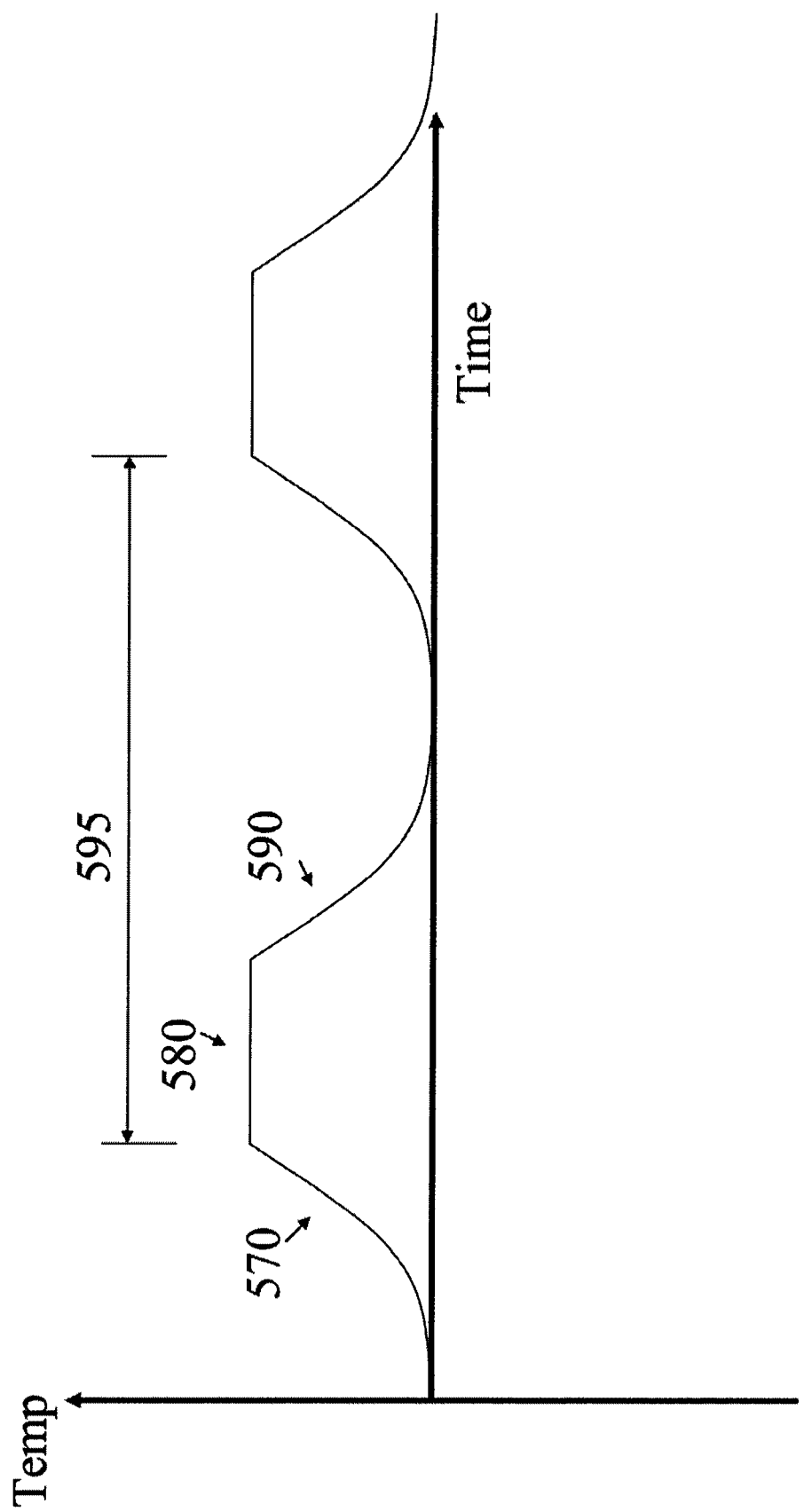
FIG. 5 is a schematic of a first embodiment of a custom temperature profile.
Figure 6:
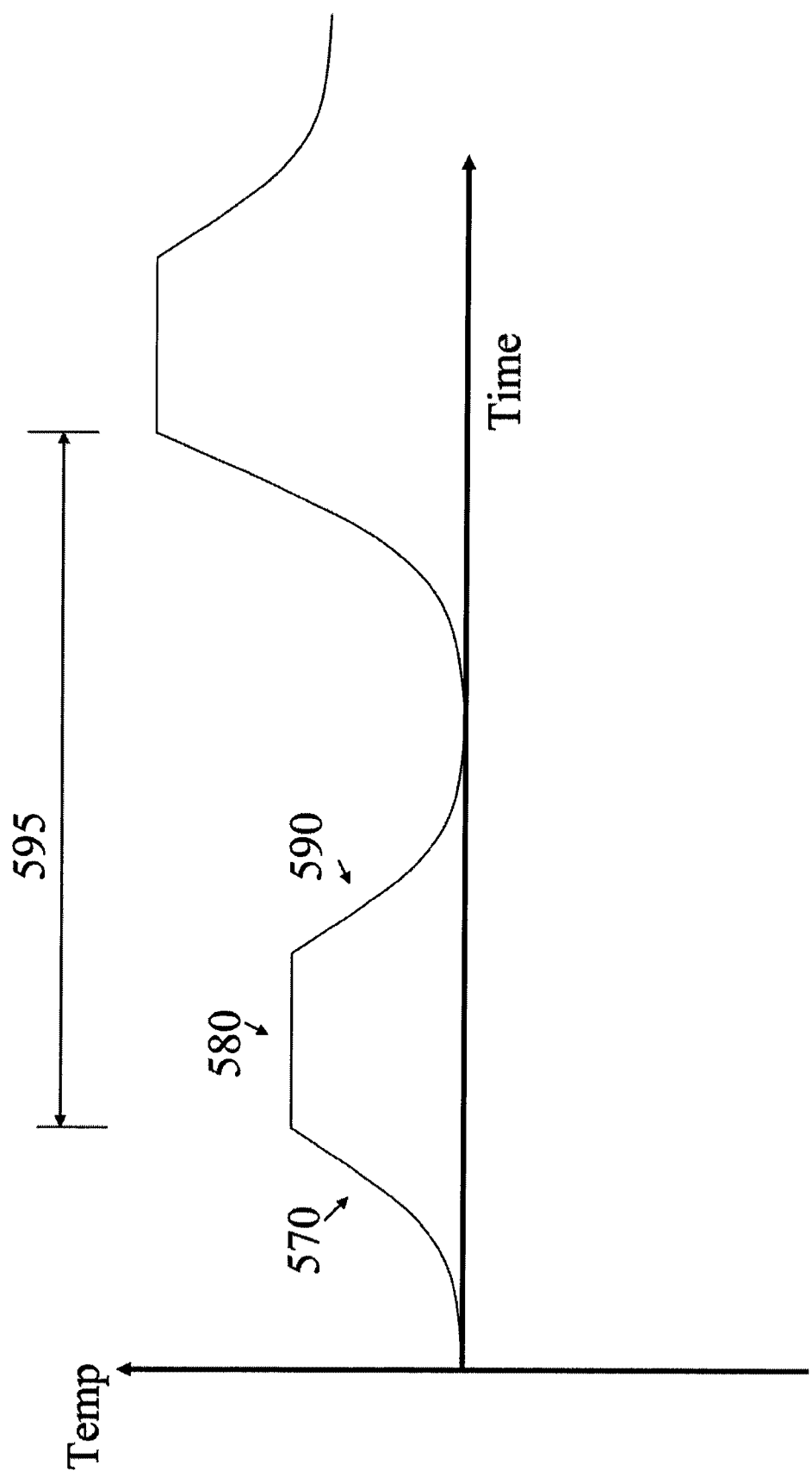
FIG. 6 is a schematic of a second embodiment of a custom temperature profile.
Figure 7:
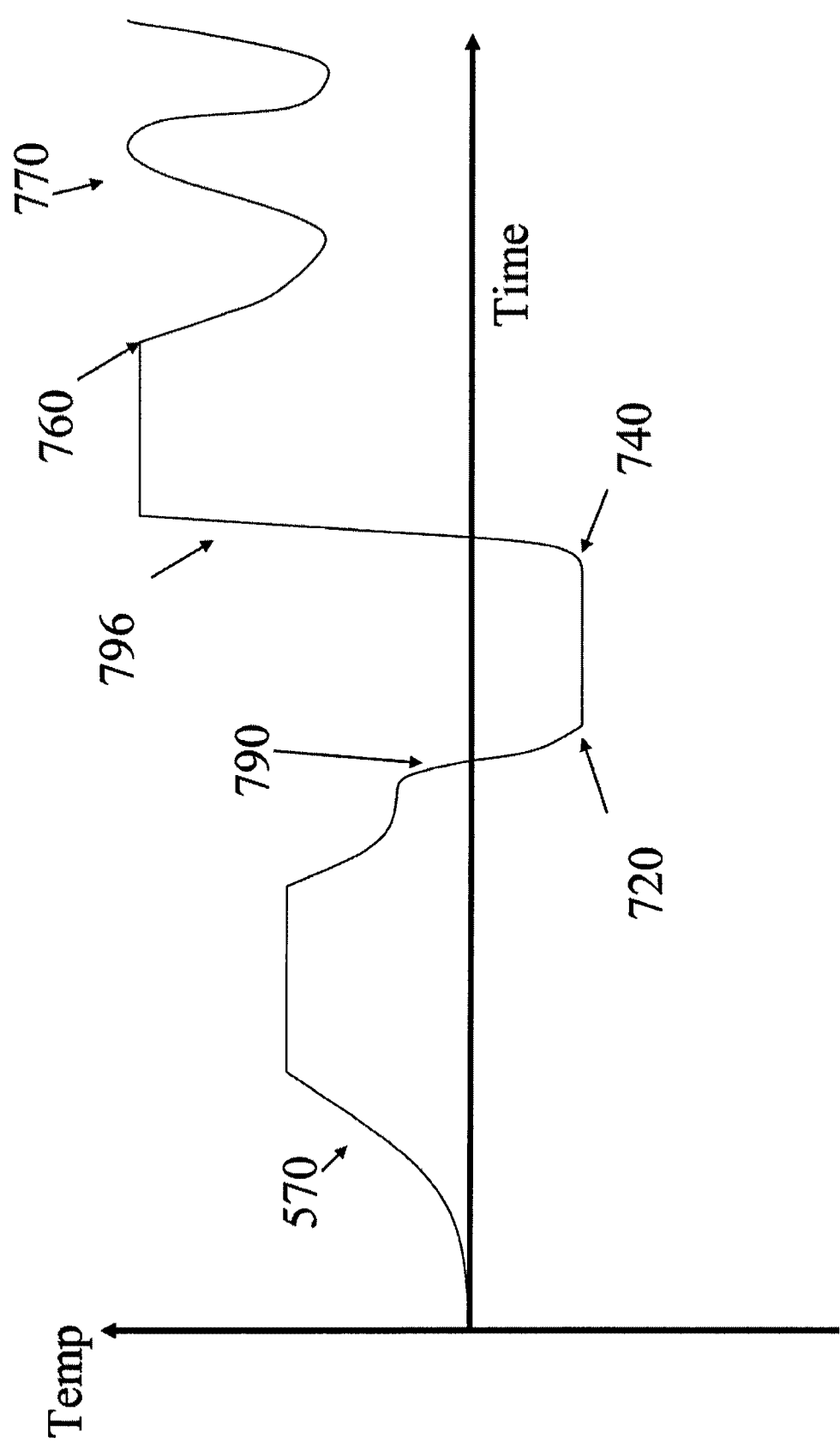
FIG. 7 is a schematic of a third embodiment of a custom temperature profile.

Referring to FIGS. 5-7, the x-axis refers to time while the y-axis refers to temperature. The intersection of the x and y-axes corresponds to ambient temperature (on the y-axis) and to "time-zero" i.e., the commencement of a first exothermic reaction (on the x-axis). As shown in FIG. 5, after a first reaction commences, the temperature begins to increase as seen at 570 until a forward phase change temperature is reached. The phase change temperature is specific to a corresponding first PCM material. At this point, the temperature profile plateaus along the left side of 580. If the first exothermic reaction is halted (either consuming the mass of one or both of the reactants or for any other reason) and the first PCM is still undergoing a first forward phase change (i.e., the solid and liquid phases are still in equilibrium) the temperature will continue to plateau along the right side of 580 until the corresponding first reverse phase change reaction ceases. At this point, all of the PCM material has been converted back to its original solid form, and the temperature begins to drop back toward ambient at 590. A second exothermic reaction may then be initiated, which causes the temperature to again rise until the phase change temperature is reached and the process repeats. The second exothermic reaction can be initiated before temperature profile 590 reaches ambient levels or after ambient temperature is reached. A period 595 between successive reactions is defined according to this profile. However, the periods between further reactions (not shown) can be different, i.e., the temperature profile does not have to be strictly periodic. Furthermore, different PCM materials can be used at different times. In the example shown in FIG. 6, the second reaction is thermally coupled to a second PCM material which has a higher phase change temperature.

To further customize a temperature profile, endothermic chemical reactions mixtures may also be used. PCM materials that are in liquid phase at ambient temperature can also be used to further the design possibilities of a customized temperature profile. The reaction of FIG. 7 initially proceeds as previously described. However, thereafter, an endothermic reaction proceeds which causes the temperature to drop faster than passive cooling, as seen by the change in slope at 790. The temperature can be driven below ambient. At 720, a forward phase change reaction of a PCM material that normally exists in liquid phase at ambient temperature commences. In this context, a "forward" reaction would be a freezing reaction. If the endothermic reaction ceases at before the forward phase change reaction completes, the temperature will continue to plateau at the phase change temperature as the solid phase begins to melt. At 740, a second exothermic reaction commences, once again raising the temperature. This reaction may comprise a different exothermic chemical reaction mixture than that used in the first reaction, as evidenced by the steeper slope of 796 as compared to 570. As the reaction progresses, eventually another phase changed happens corresponding to a third phase change temperature. At 760 the phase change reaction ceases and the temperature drops back toward ambient. At 770, additional exothermic and/or endothermic reactions may be modulated without using PCM materials. Therefore, there will not be any temperature plateaus in region 770. The temperature profile of FIG. 7 is not intended to describe a specific embodiment; rather it is intended to illustrate many of the products and processes that can be combined in various ways in order to achieve virtually any desired temperature profile. If the chemicals and PCM materials are pre-packaged according to a set design, all a user has to do is initiate the first reaction (for example, by simply peeling off a tape or backing) and no further instrumentation or outside power sources are necessary.

Figure 8:
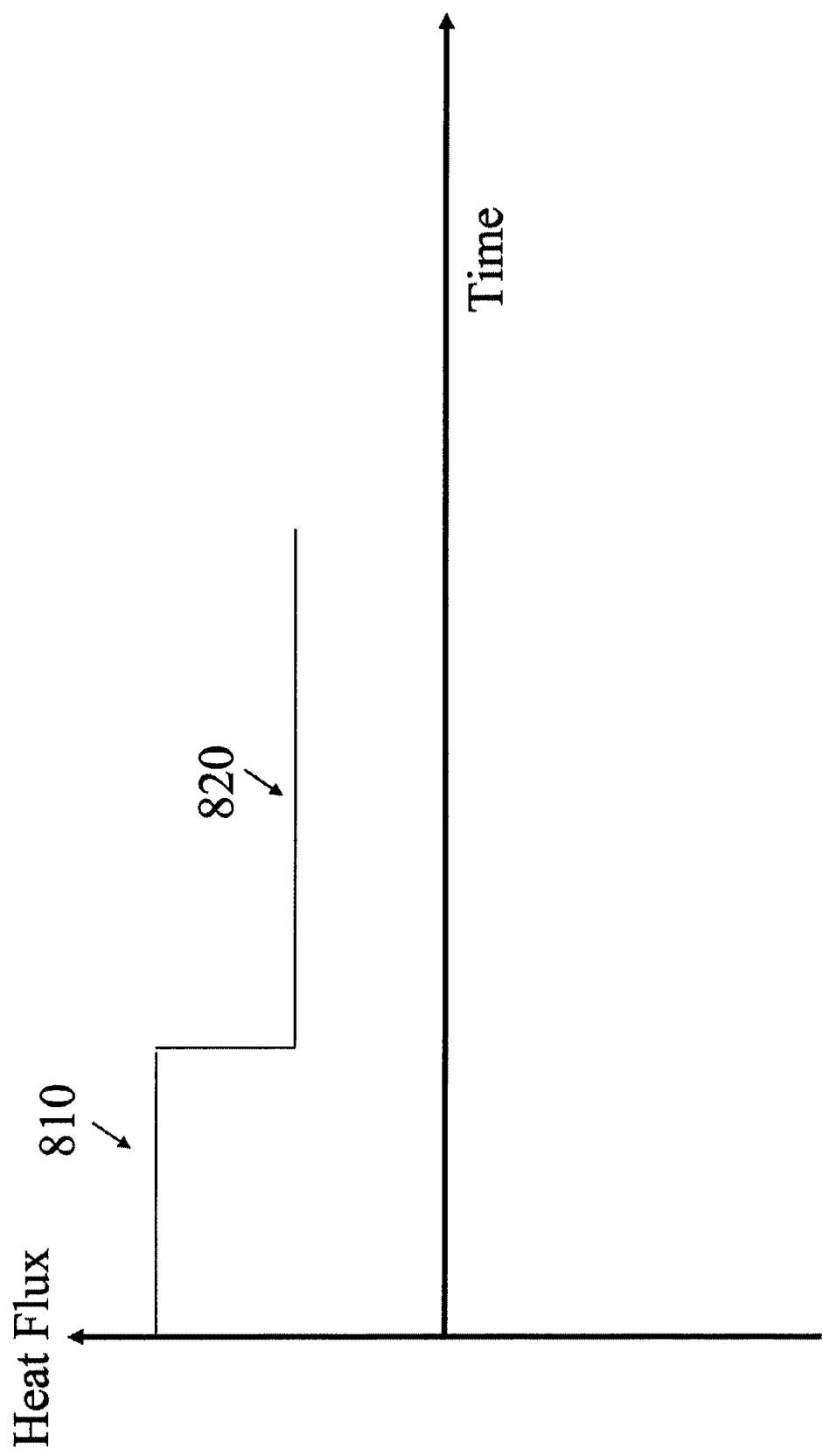
FIG. 8 is a schematic of an embodiment of a custom heat flux profile.

In another embodiment, shown in FIG. 8, two or more chemical reactions can be initiated simultaneously, thereby providing a large initial input heat flux 810. After a time, one or more of the initial chemical reactions is allowed to cease, while one or more of the reactions continues, thereby providing a smaller input heat flux 820 for the remainder of the reaction. In this way two or more different temperature profiles can be achieved, while only requiring a single initiation.

Figure 9:
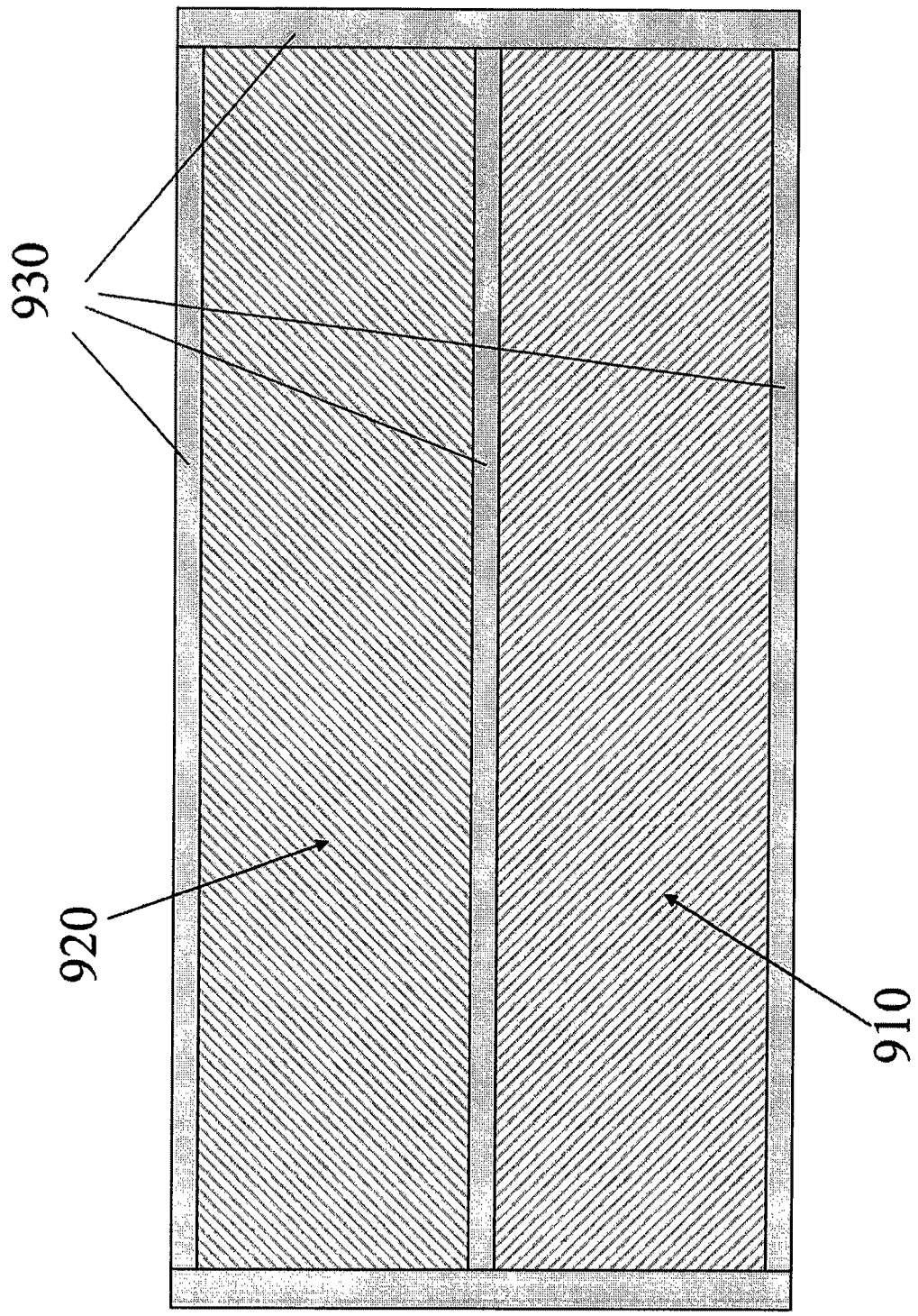
FIG. 9 is a schematic of a two-layer chemical heating element.

In an embodiment shown in FIG. 9, the ECRM materials can be separated from the PCM using a two-layer design. The chemicals on the lower layer 910 are separated from the PCM on the upper layer 920 by a material 930. Suitable materials are aluminum foil, copper foil, plastic or the like. Alternatively, the PCM can be introduced into the system by encapsulating the PCM in carbohydrate spheres and mixing it with the ECRM materials. This one-layer embodiment (not shown) may also be enclosed by aluminum foil, copper foil, plastic or the like. Similarly, in the case of an ECPCM, the ECPCM may be enclosed by aluminum foil, copper foil, plastic or the like.

Applications of Chemical Heating to PCR

Having described exothermic (or endothermic) chemical heaters utilizing phase change materials, several embodiments of diagnostic platforms suitable for PCR incorporating ECRMs and PCMs will now be described. This disclosure describes a completely non-instrumented diagnostic platform based on nucleic acid amplification. An embodiment of the diagnostic device described herein will enable the replacement of an entire class of diagnostic devices with one that is several orders of magnitude more sensitive, and thus will allow much more appropriate intervention in settings with limited resources. In an embodiment, the device combines immunochromatographic strip technology, for detection of amplified nucleic acid, with exothermic chemical heating (and/or endothermic chemical cooling) and passive fluid recirculation in microchannels for nucleic acid amplification. The amplicon detection is based on introducing immunologically detectable labels during the amplification process, coupling the amplicons to visually detectable particles, and immunocapturing the particles on the detection portion of the immunochromatographic strip. A secondary control target, amplified concurrently with the analytical target, will also be captured and visualized on the same strip, and will act as a check to ensure that the sample has undergone complete amplification and detection. The device will be low-cost, disposable, have no moving parts, and will look, feel, and be read very similarly to ICS cassette devices. With this platform, it will be possible to perform highly sensitive and specific PCR assays in areas that so far were limited to ICS technology, and thus provide the basis for early detection and rapid intervention for many common and deadly pathogens, by making affordable, more accurate, diagnostics of infectious diseases available to millions of people in developing countries.

Figure 10:
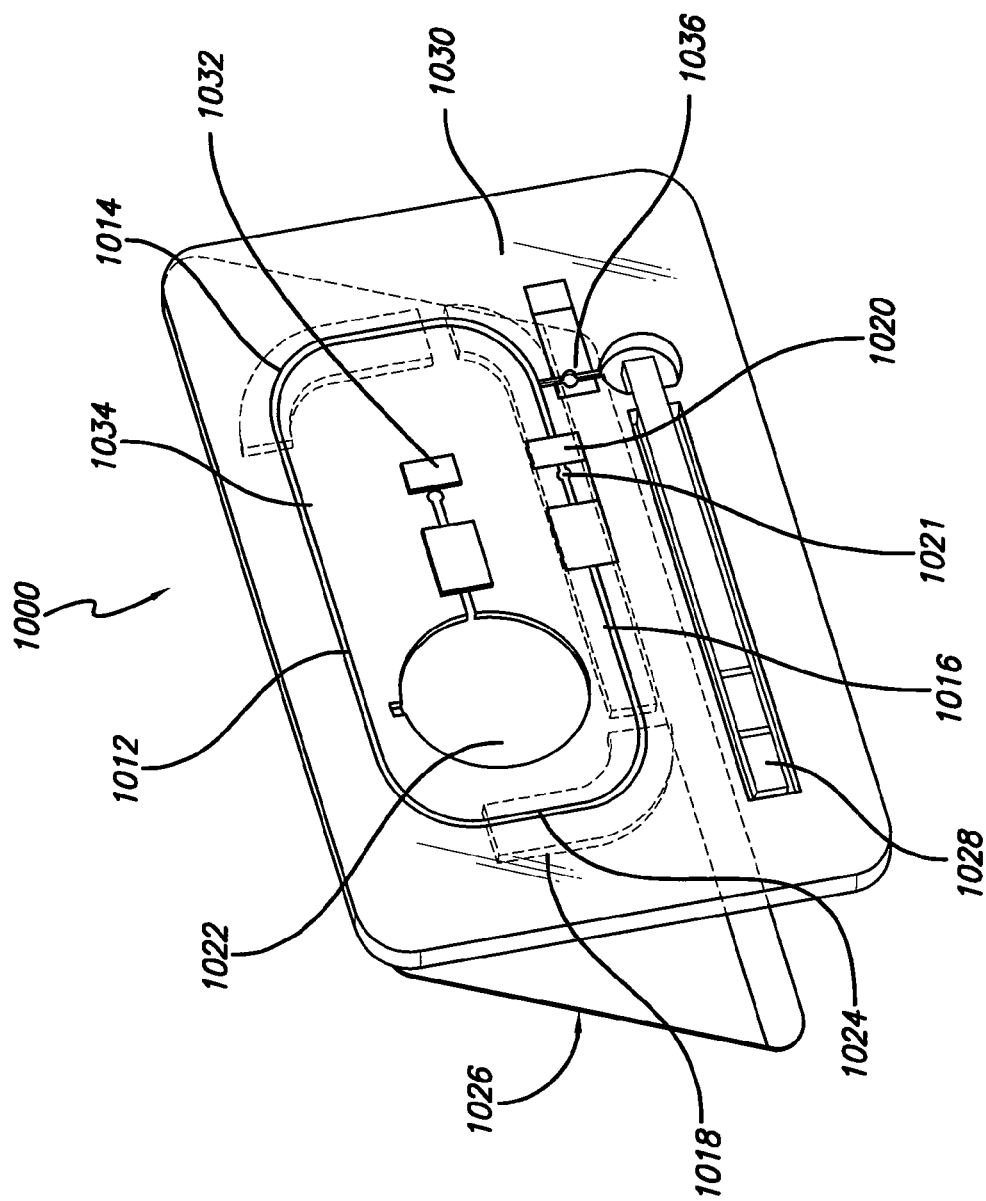
FIG. 10 is a forward perspective view of an exothermal chemical PCR device.

Two exemplary embodiments of non-instrumented heat cyclers will be described, with reference to FIGS. 10-11. The first, Exothermal Circulation PCR (ECPCR) 1000 is based on the circulation of a liquid in an upright, closed-loop channel that is heated though exothermal heat pads to different temperature levels at different locations along the channel. The circulation is induced by the resulting differential in density of the liquid portions that are at higher and lower temperatures. The second variant, Linear Exothermal PCR (LEPCR) 1400 will heat cycle a liquid that is wicked repeatedly through a channel over exothermal heat pads by the sample pad of a lateral flow strip (LFS) that will detect the amplicons generated during the heat cycling.

ECPCR

The ECPCR design 1000 has a closed-loop reaction channel 1012 of constant or varying cross-section geometry thermally coupled with chemical heat transfer zones 1014, 1016, 1018. To begin the test, sample inlet tape 1020 is first removed. The 50 µL (for example) sample is then pipetted into the channel 1012 at inlet 1021 and fills the entire closed-loop volume. Excess sample can overflow into the prefilled buffer well which also serves as an expansion volume. The sample will reconstitute with a PCR master mix 1024 of primers, uNTP, and TAQ polymerase which is prestaged in the denaturation zone 1018. The back panel of the card 1026 is then peeled back to activate the heat zones 1014, 1016, 1018 and angled as a support to establish the required vertical orientation of the card which in turn sets up a thermal driving head and induces natural circulation. As the sample flows, a representative slice of sample moves over each PCR temperature zone: 94° C. for denaturation 1018, 55° C. for annealing 1014, and 74° C. for extension 1016. After approximately 35 cycles or revolutions around the closed-loop channel, amplification is complete, and the sample is ready to be transferred to the LFS/ICS 1028. The temperatures mentioned above are example target temperatures. In one embodiment heat zone 1018 may be kept within a narrow limit, for example, 94° C.+/−2° C. (i.e., 92° C.-96° C.) In one embodiment, heat zone 1014 may be kept within the range 53°-70° C., preferably at 55° C.+/−2° C. (i.e., 53° C.-57° C.).

In order to help keep the three heat zones 1014, 1016, and 1018 at distinct temperatures, insulation (not shown) may be used. Urethane foam, besides being an excellent insulator, is also cheap and easy to incorporate into various devices. Alternately, any material having a relatively low heat transfer coefficient may be used. Since heat transfer is a surface phenomena, it is also advantageous to use geometries having low surface to volume ratios, for example, spherical or cylindrical geometries. Insulators and geometry should be used to best advantage whenever temperature and/or heat flux is to be controlled (i.e., in diagnostic applications other than PCR).

To provide a path for the sample to flow to the ICS well, the flow strip gate tape 1030 is removed along with the gate 1036. The buffer well vent is then opened by removing the buffer vent tape 1032. The user puts his thumb over the buffer vent well 1034 and then depresses the buffer thumb pump 1022 forcing buffer through the reaction channel 1012 and pushing the sample and buffer into the ICS well where it is then wicked into the LFS. The user then removes both thumbs from the card to allow the buffer well to vent without drawing buffer back into the well.

In contrast to forced circulation, which relies on the head energy provided by pumps, natural circulation results from the different densities of relative cold and heated portions of a closed-fluid system. Natural circulation does not require the energy of any mechanical devices. The simplicity of this circulation mode and minimal parts required in the design is an ideal approach to an inexpensive, disposable, PCR diagnostic device.

The ECPCR design takes into consideration the three requirements for natural circulation: a temperature differential (i.e., a heat source and a heat sink), the heat source is at a lower elevation than the heat sink, and the fluids are in contact with each other. The heat source may be the heating element and the heat sink may be an area outside of the heating element. Additionally, since pressure head losses are increased by tortuous flow paths and sharp angles in the fluid channel, the microfluidic design will necessarily avoid these in order to provide optimal channel velocity and therefore minimum cycle time.

Figure 12:
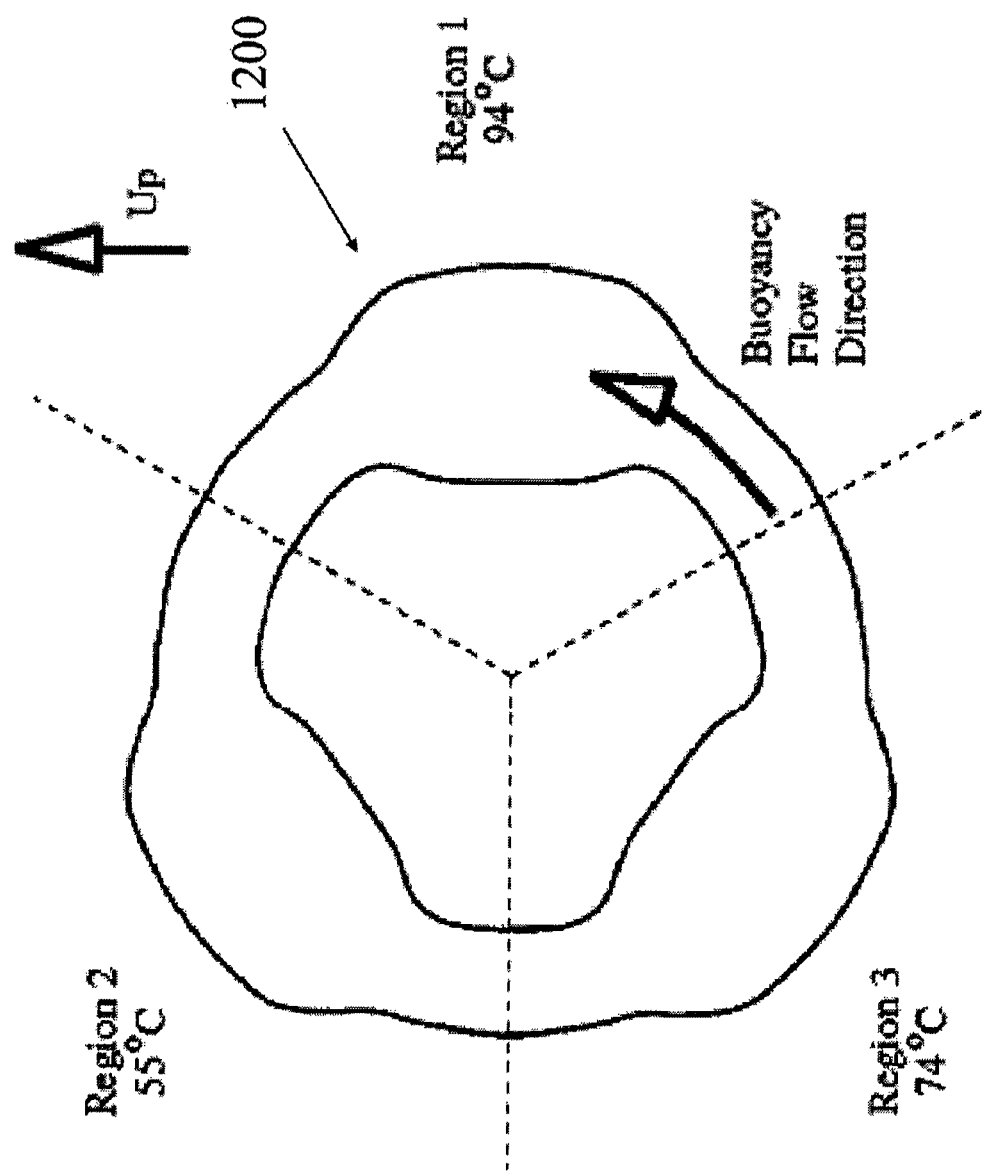
FIG. 12 is a perspective view of a model of thermal convection.

In order to demonstrate the fundamental feasibility of ECPCR, a simplified modeled version 1200 of the circuit is described and shown in FIG. 12. The following calculations demonstrate that PCR cycle times of 8 seconds are possible with a simple, card-based natural circulation system. For modeling purposes an annular shape for the PCR cycler channel is assumed. However, other shapes such as triangular or circular channels can be modeled using the same process.

An annular shape filled with fluid can be driven in a rotating flow by density variations within the fluid. In aqueous solutions, density varies inversely with temperature. The density variation leads to a buoyancy force that can be utilized to create a rotational flow within the device. Rotational speed can be precisely controlled by controlling the temperature in each region of the device.

Figure 20:
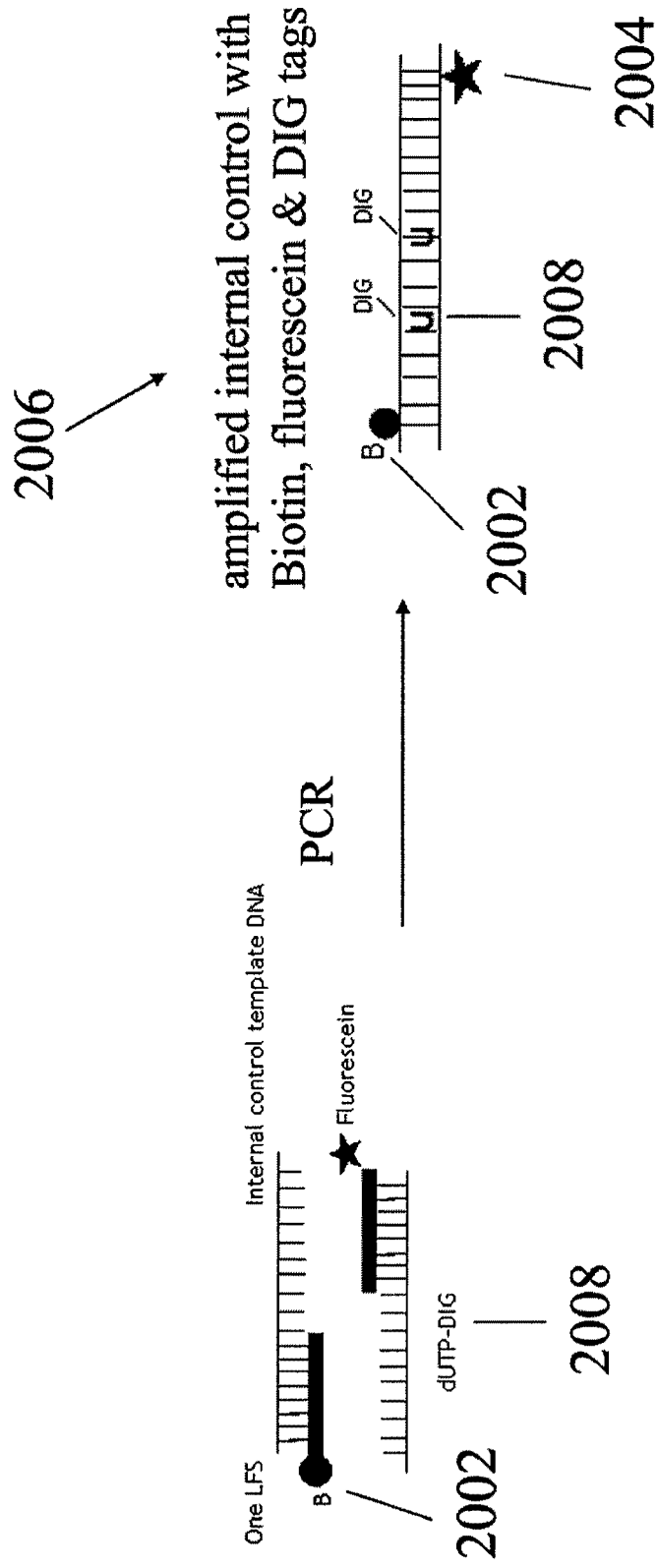
FIG. 20 is a schematic of an internal control DNA sequence being labeled by a fluorescein tag and biotin.

To determine the appropriate geometry for target cycle times of the solution, it is assumed that the device quickly reaches steady state operation, a reasonable assumption for a micro-scale device. The target flow rate is very slow and can be considered Stokes flow for computational purposes. The Boussinesq approximation can be used to determine buoyancy force per volume of fluid, B, which is $$B = \rho g \alpha \Delta T \quad \text{(equation 1)}$$

in which p is the fluid density, g is the acceleration of gravity, $\alpha$ is the thermal expansion coefficient of the fluid, and $\Delta T$ is the temperature difference using the temperatures given in FIG. 20. The residence time, t, in each region can be determined from the fluid flow rate Q and the volume V of each region $$t = V/Q \quad \text{(equation 2)}$$

The rotating fluid flow is created by the buoyancy force acting over the cross-sectional area, A, of the connecting channel and forming a driving pressure, P, $$P = RQ = BV/A \quad \text{(equation 3)}$$

in which R is the flow resistance of the interconnecting channels. The fluid resistance in a rectangular channel is $$R = \frac{128 \mu L}{4 h w F_{AR} D_H^2} \quad \text{(equation 4)}$$

in which $\mu$ is the dynamic viscosity of the solution and L is the length of all connecting channels. The aspect ratio factor $F_{AR}$ represents the effect of channel cross-section shape on flow resistance in a rectangular channel and is given approximately by equation 5, which is accurate within 2%.

$$F_{AR} = \frac{2}{3} + \frac{11}{24} \frac{h}{w} \left(2 - \frac{h}{w}\right) \quad \text{(equation 5)}$$

The hydraulic diameter $D_H$ of a rectangular channel is $$D_H = \frac{2}{1/w + 1/h} \quad \text{(equation 6)}$$

By substitution of Equation 3 into Equation 2, the residence time of the solution in each region can be estimated from $$t = R \, A/B \quad \text{(equation 7)}$$

The above equations can be used to design the geometry of the EPCPR device in order to target desirable velocity and residence times of the solution. The fluid velocity and residence time of the solution in each region are controlled by the dimensions of the annulus. Increasing the thickness dimension increases the fluid velocity and decreases the residence time in each region.

Figure 13:
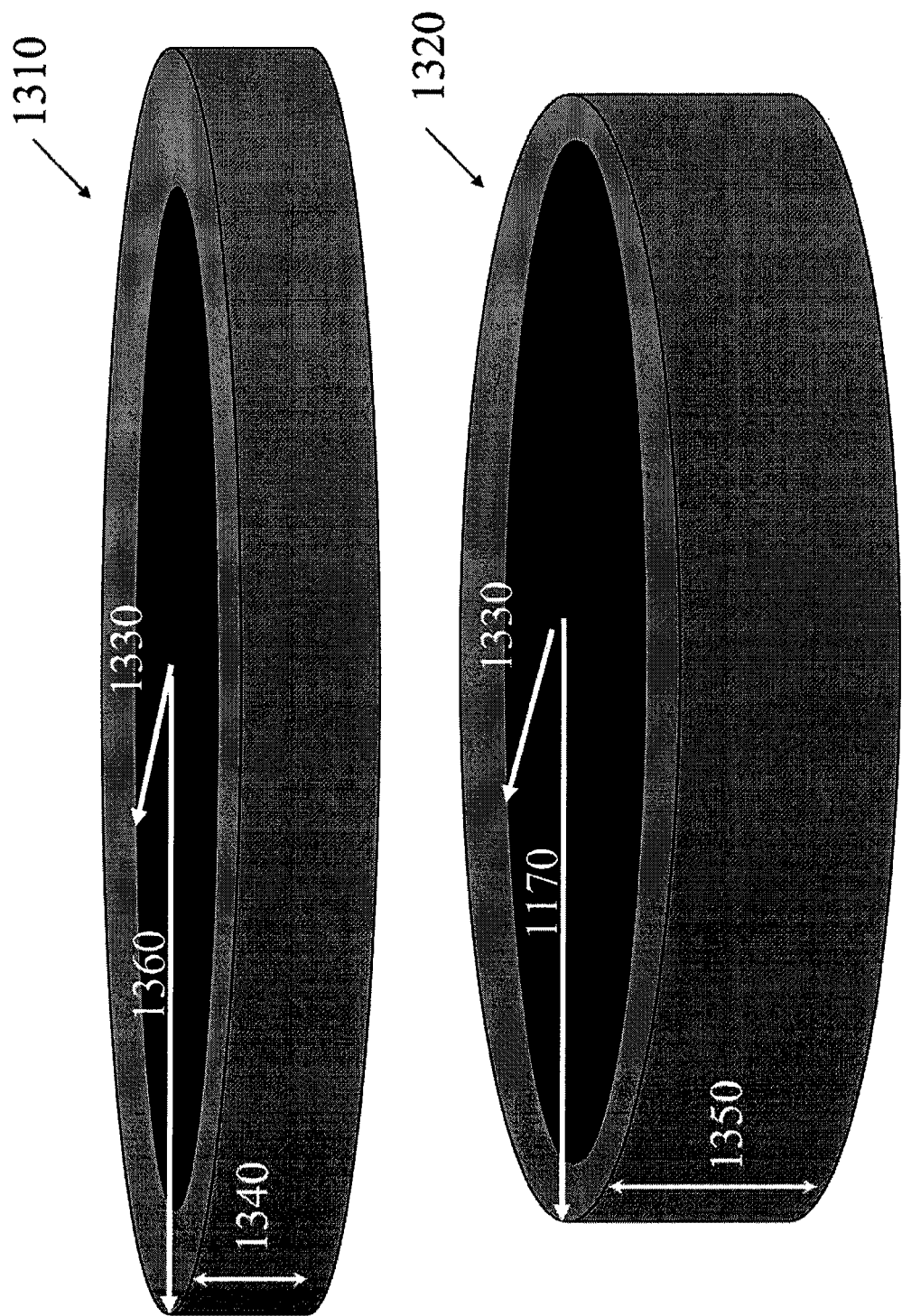
FIG. 13 is a schematic of variants of the model of FIG. 12.

Table 1 lists three potential annular shapes. Variant 1 is shown as 1310 in FIG. 13, while variant 3 is shown as 1320. The inner diameter 1330 is the same (8 mm) in each variant. The thickness 1140 of variant 1 is less than the thickness 1350 of variant 3. To keep the volume constant, the outer diameter of variant 1 1360 is larger than the outer diameter 1370 of variant 3. Variant 2 (not shown) is an intermediate design.

TABLE 1

| Design Variant | Volume of fluid, μL | Residence time in each region, sec | Time for one cycle, sec | Thickness of fluid annulus, mm | Outer diameter of fluid annulus, mm |
| --- | --- | --- | --- | --- | --- |
| 1 | 36 | 8.0 | 36.0 | 0.32 | 16.0 |
| 2 | 39 | 3.5 | 16.0 | 0.50 | 14.0 |
| 3 | 39 | 1.7 | 8.0 | 1.00 | 11.4 |

LEPCR

Figure 14:
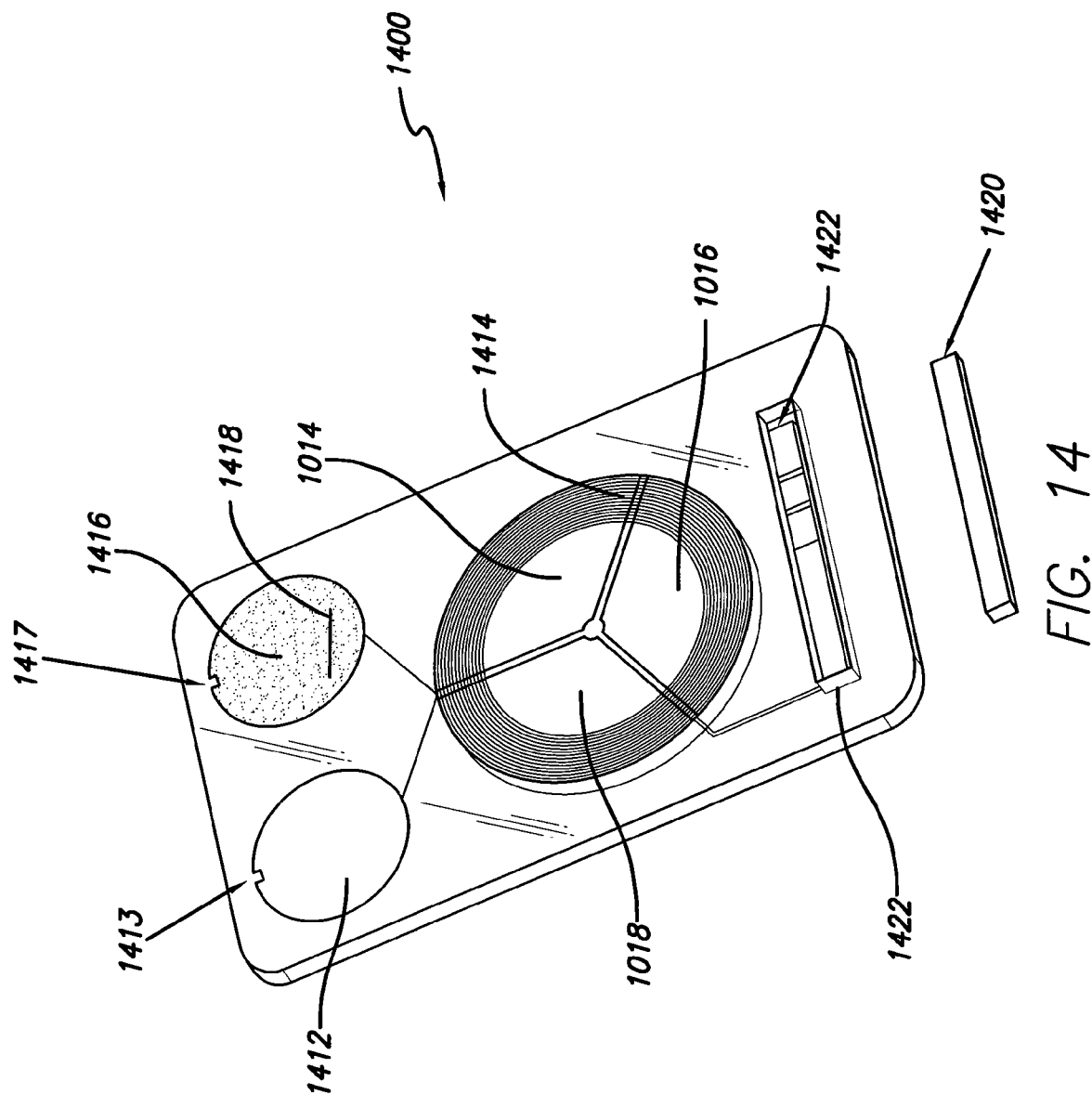
FIG. 14 is a forward perspective view of a linear exothermal chemical PCR device.
Figure 15:
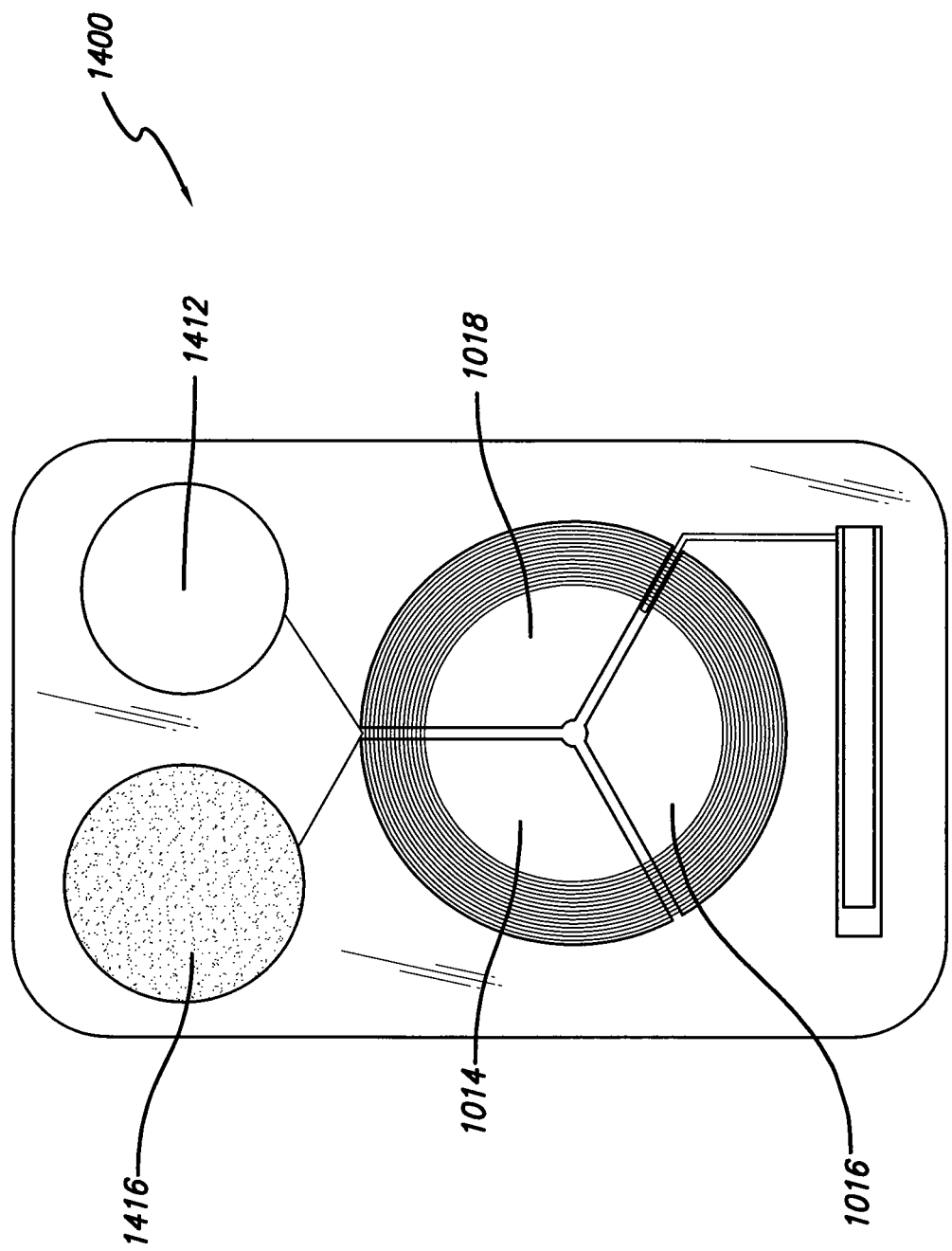
FIG. 15 is a reverse perspective view of the linear exothermal chemical PCR device of FIG. 14.
Figure 16:
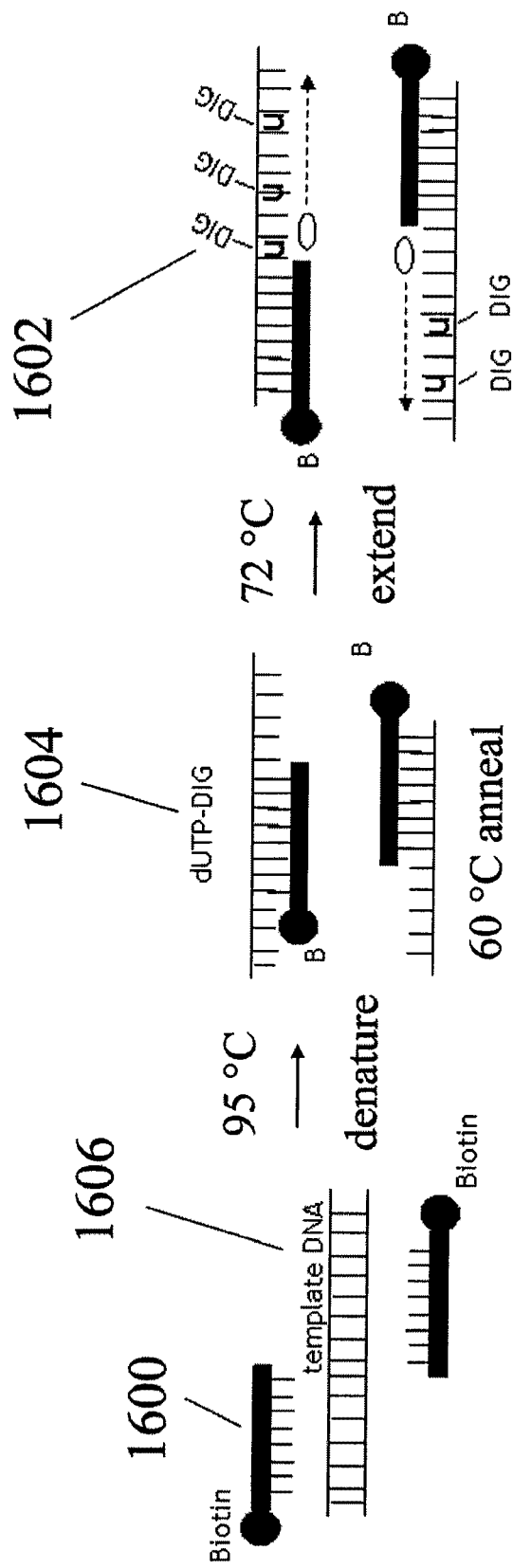
FIG. 16 is schematic of a DNA labeling technique.
Figure 17:
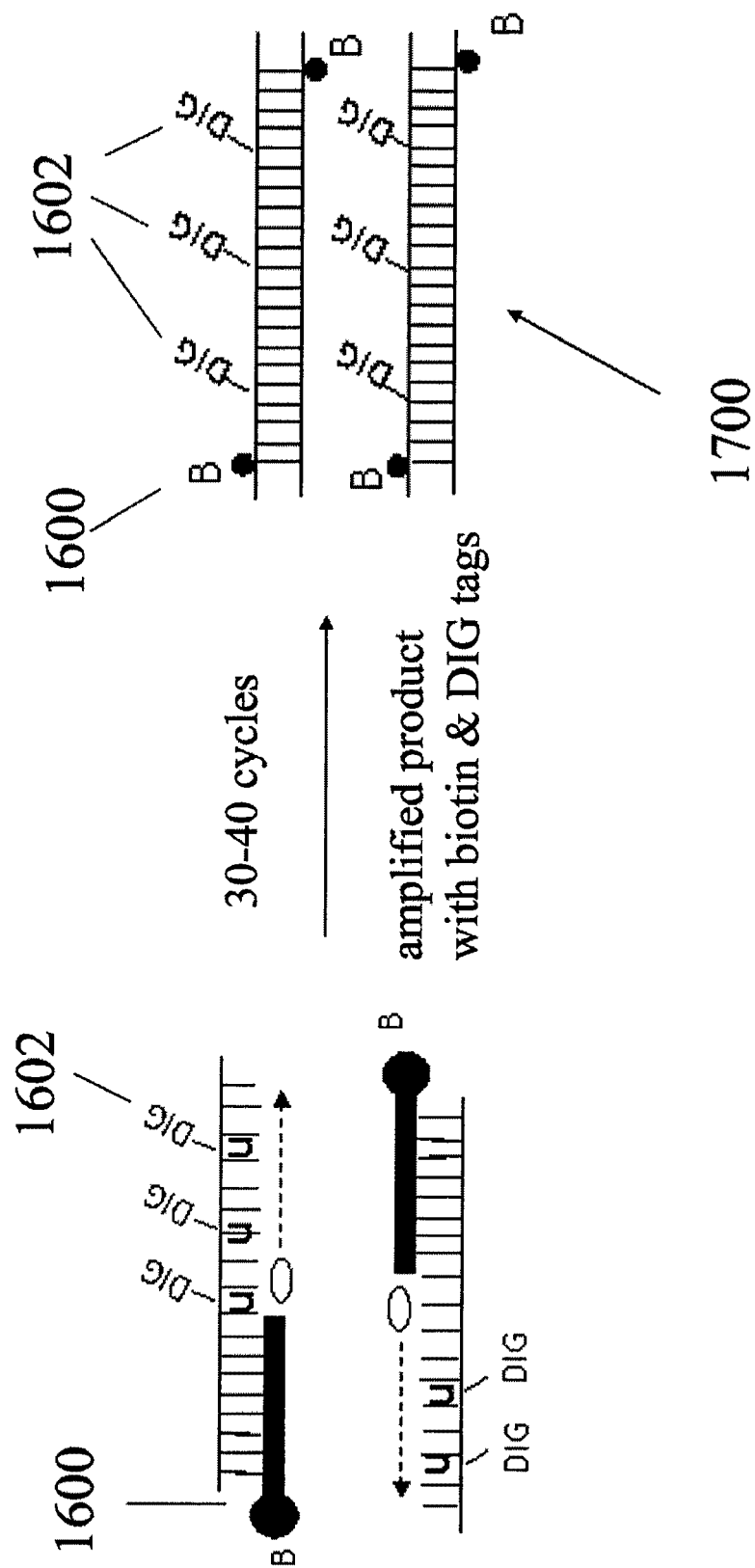
FIG. 17 is a schematic of amplifying the DNA of FIG. 13 using PCR cycles.
Figure 18:
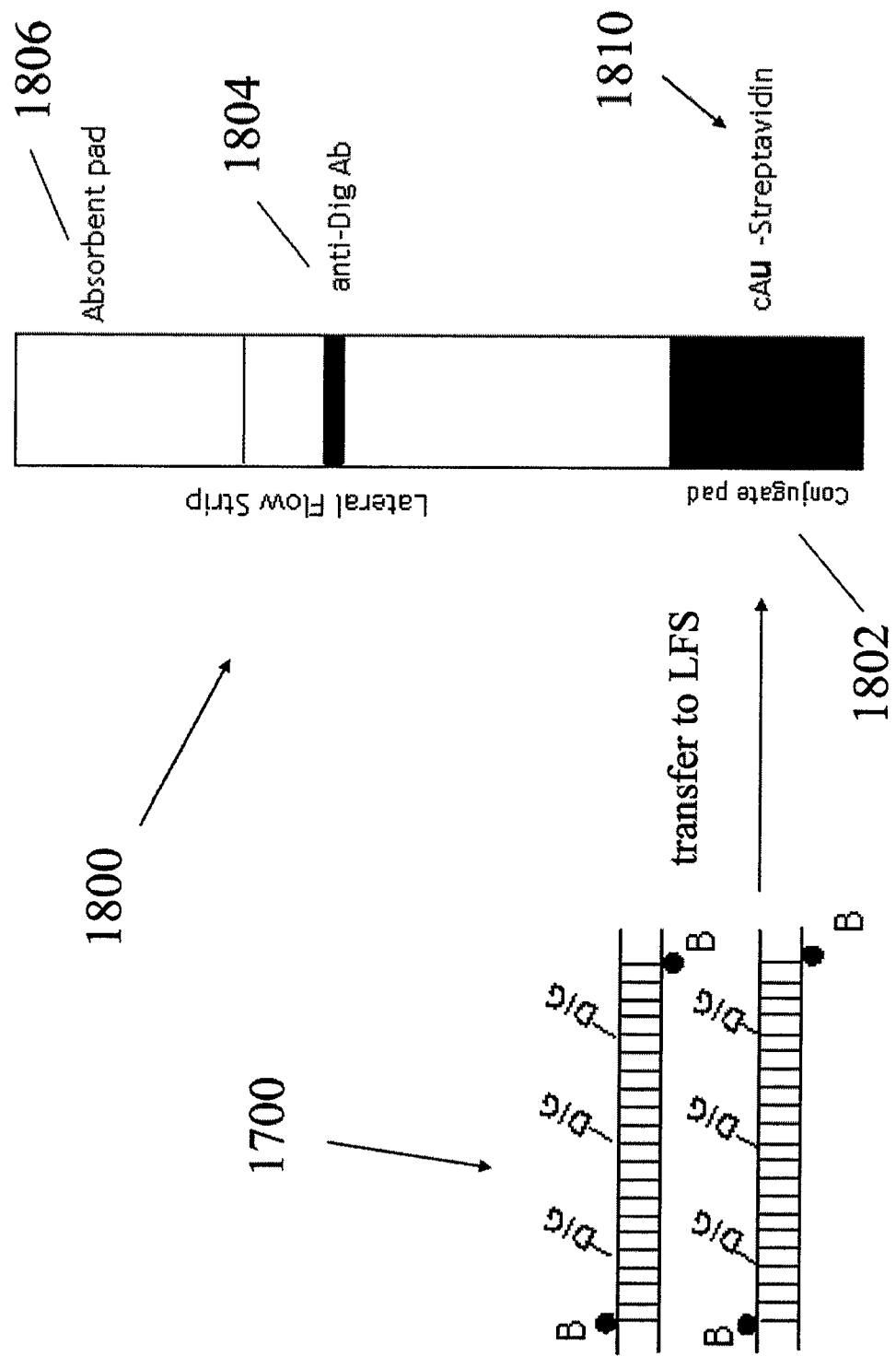
FIG. 18 is a schematic of the lateral flow strip used to detect the labeled DNA of FIG. 16.
Figure 19:
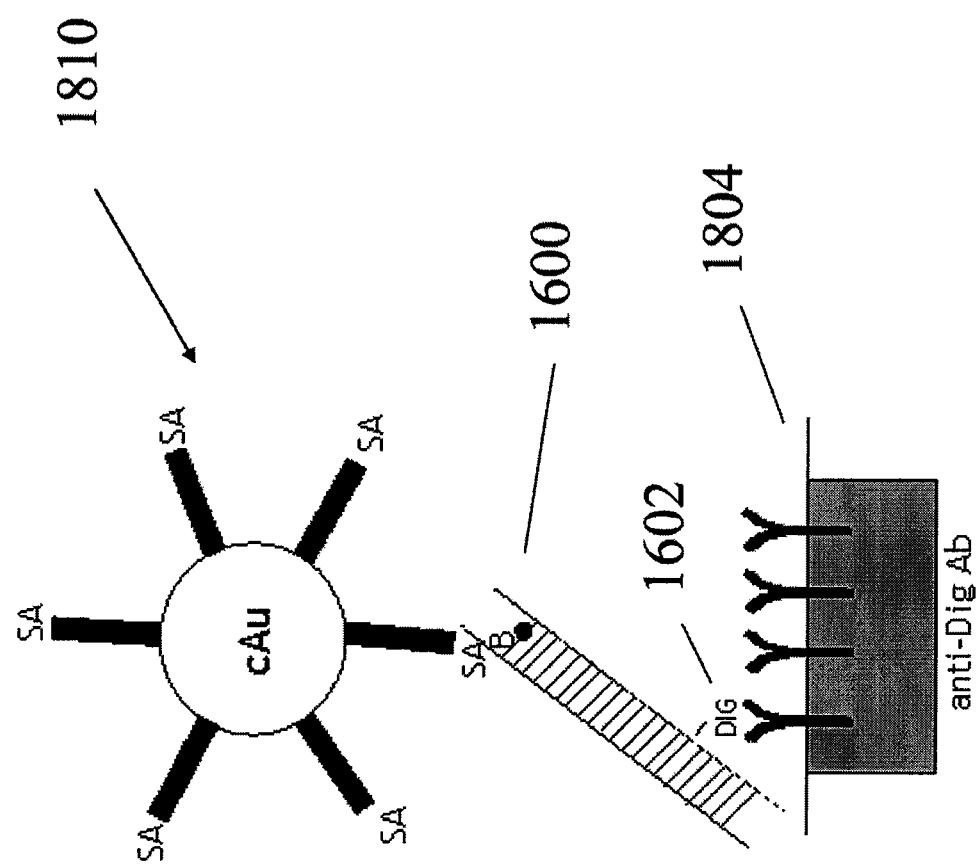
FIG. 19 is a schematic depicting the binding of the DNA on the lateral flow strip of FIG. 18.

The LEPCR design, shown in FIGS. 14 and 15, is an alternative configuration of a low-cost PCR card with ICS detection and again relies upon chemically driven heat zones (and possibly also chemical cooling zones) for each PCR process. To ensure the lowest possible cost of the device, no moving parts are involved in the reaction channel. Movement of the sample is through capillary and wicking forces only.

The user initiates the test by removing the back cover (not shown) of the card to agitate and/or expose the heating chemicals. The back cover stub acts as a stand to allow air to interface with the chemicals and creates a slight pressure head due to gravity. With the card on a table, the user pipettes a volume of wetting buffer into the buffer well 1412 via entry 1413. The buffer is then drawn into and completely wets the spiral channel. This step is required to ensure the sample movement throughout the spiral channel is due to wicking forces and not due to capillary forces thereby establishing a more steady flow rate. The user then pipettes a volume of sample into the preheated (94° C.) sample well 1416 via entry 1417. In one embodiment, the wetting buffer well and sample well comprise a 19 mm circular cross section 0.3 mm deep, for a volume of 50 μL. The spiral channel can also be 50 μL, comprising 30 passes (with only 20 shown for clarity in FIG. 14) with a width and depth of 0.25 mm. This preheated well promotes reconstitution and mixing of the master mix of primers, dUTP, and TAQ polymerase. It also extends the initial denaturation time of the first cycle and may allow for longer initial incubation to perform reverse transcriptase as required by specific virions such as MS2 (Venezuelan equine encephalitis).

After reconstitution and mixing, a sacrificial flow strip 1420 is inserted into the flow strip well 1422. As the strip wets with wetting buffer, the sample is drawn through the spiral reaction channel 1414 while continuously cycling through the three PCR zones. The sample undergoes one PCR cycle per revolution. Once the sample is completely contained in the spiral channel, the user removes the saturated sacrificial flow strip 1420 and replaces it with a test strip 1422 with colloidal gold control and indicator stripes, as will be discussed below. The resultant wicking forces from the dry test strip in contact with the wet channel draw the sample through the spiral, completing the 30 cycles and initiating take-up in the test strip. An additional, user-added 100 μL (50 μL each to the buffer and sample wells) washes the channel and acts as a running buffer as it is also drawn into the test strip.

The spiral channel has advantages over a serpentine channel. In the three-zone serpentine configuration the sample travels through a serpentine channel over three parallel temperature zones. In this configuration, extra time is unnecessarily spent in the middle zone. This increases cycle time (two serpentine two cycles=94/55/74/55/94/55/74 involves 7 zone passes whereas a two spiral cycles 94/55/74/94/55/74 involves only 6 zone passes to complete 2 cycles). This should save 15% on total reaction time and minimizes the bends and complexity of the channel. A potential drawback to the spiral channel configuration is that there is a slight decrease in time per cycle as the channel spirals in. This can be minimized using the smallest channel width and spacing.

The spiral channel geometry shown in FIG. 14 is a simple representation. The actual channel geometry can be developed to control the flow such that the dwell in any one zone is optimized for PCR efficiency. Channel widths can be increased to increase the volume and thereby the amount of time in any one zone. Alternatively, the zones, which are shown to have equal area on the card, may be nonequivalent to adjust for required zone dwell times. The represented channel (as well as all the base card features) can be CNC machined in Mylar (polyethylene terephthalate) using standard square end mill tools. Other materials can also be used based upon their dimensional stability and whether they have residues that inhibit the polymerase.

Exothermal heating wells are prefilled 1.9 mm deep from the back of the card with a homogeneous mixture of exothermic chemicals and phase-transition material (spherical carbohydrate shell surrounding temperature-specific phase transformation material such as wax or a thermoplastic polymer). The exact mixture and chemistry is specific to the PCR stage to maintain a stable temperature during the reaction process: 94° C. for denaturing, 55° C. for annealing, and 74° C. for extension. The temperatures mentioned above are example target temperatures. In one embodiment denaturing occurs at, for example, 94° C.+/−2° C. (i.e., 92° C.-96° C.) In one embodiment, annealing occurs at 53°-70° C., preferably at 55° C.+/−2° C. (i.e., 53° C.-57° C.). Although a 3-temperature PCR configuration is shown, it is also possible to get acceptable amplicon replication with a 2-temperature PCR. Therefore, the design may be simplified with only 2 temperature zones. Alternatively, there could be 4 or 6 temperature zones (2-temperature and 3-temperature PCR respectively), whereby the sample undergoes 2 cycles of amplification for each spiral revolution in the reaction channel. The ECPCR embodiment could also employ a number of heat zones other than three.

Instead of (or in addition to) the wicking forces described above, a syringe could be used to provide a substantially constant flowrate. For example, a spring driven infusion pump, such as the one sold by Go Medical Industries Pty. Limited under the name SPRINGFUSOR®, (http://www.go-medical.com.au/products/springfusor.php) could be adapted to the diagnostics described herein. A spring-loaded syringe-like pump (like the SPRINGFUSOR® or similar) can provide a substantially constant flowrate. These types of pumps are used in IV infusion, where the flowrate tolerances are on the order of +/−10%. For diagnostic applications, the exact flowrate is not as critical because the flow throughout the channel cross section is not constant.

Lateral Flow Strips for Amplicon Detection

Detection of nucleic acids (NA) on the LFS will be achieved by first labeling the nucleic acids during PCR, then utilizing standard lateral flow technology to capture the labeled amplicons. Lateral flow strip is an ICS embodiment suitable for rapid tests of infectious diseases for low-resource settings. This test platform has attractive performance attributes for developing-world applications including use of relatively inexpensive off-the-shelf components and reagents, the ability to format the tests for detection of antigens or antibodies, its usability with a wide range of specimens (e.g., exudates, swabs, urine, serum, plasma, or blood), and its stability without refrigeration.

For optimal impact in developing countries, simple and rapid tests are needed that are economical for widespread use. The target characteristics of field-appropriate tests include: cost, simplicity, rapidity, convenience, stability, and accuracy. Tests must be cost-effective and affordable to public sector programs, with a reasonable and sustainable profit margin for the producer at an economical scale of production. To use the tests properly, minimal training and basic or no equipment should be necessary. If used for diagnosis, results should be available before the patient leaves the clinic—preferably in 10 to 15 minutes or less. Specimens should be easy to collect, culturally acceptable, and with minimal preparation or pretreatment. For potential use in the field or stockpiling at regional centers, the assay should have a long shelf life (one to two years) at ambient temperature. Finally, the tests should be accurate, i.e., appropriately sensitive, specific, and able to discriminate past from present (acute) infections. An amplicon detection strip, in conjunction with a low-cost, fast, and simple PCR thermal cycler according to the present invention, can create a diagnostic that has the cost and ease of use advantages of a ICS test, but with the sensitivity and specificity advantages of PCR.

The basic NA labeling and detection sequence is shown in FIGS. 16-19. Nucleic acids 1606 will be double labeled during PCR with both biotin 1600 and digoxygenin (DIG) 1602. For biotin labeling, PCR primers prelabeled at the 5' end with biotin are employed. These prelabeled primers can be custom ordered from most oligonucleotide suppliers or unlabeled primers with amino linkers can be biotinylated in house using commercial biotin conjugation kits. An example commercially available kit is from Roche, product number 1008960. To label amplicons with DIG, a quantity of dUTP-DIG will be included in the reaction mixture and the DIG-labeled nucleotide will be incorporated into the PCR product. dUTP-DIG is commercially available from Roche, product number 1093088. Biotinylated primers and dUTP-DIG reagents are pre-measured and dried down on the miniaturized PCR device.

Figure 11:
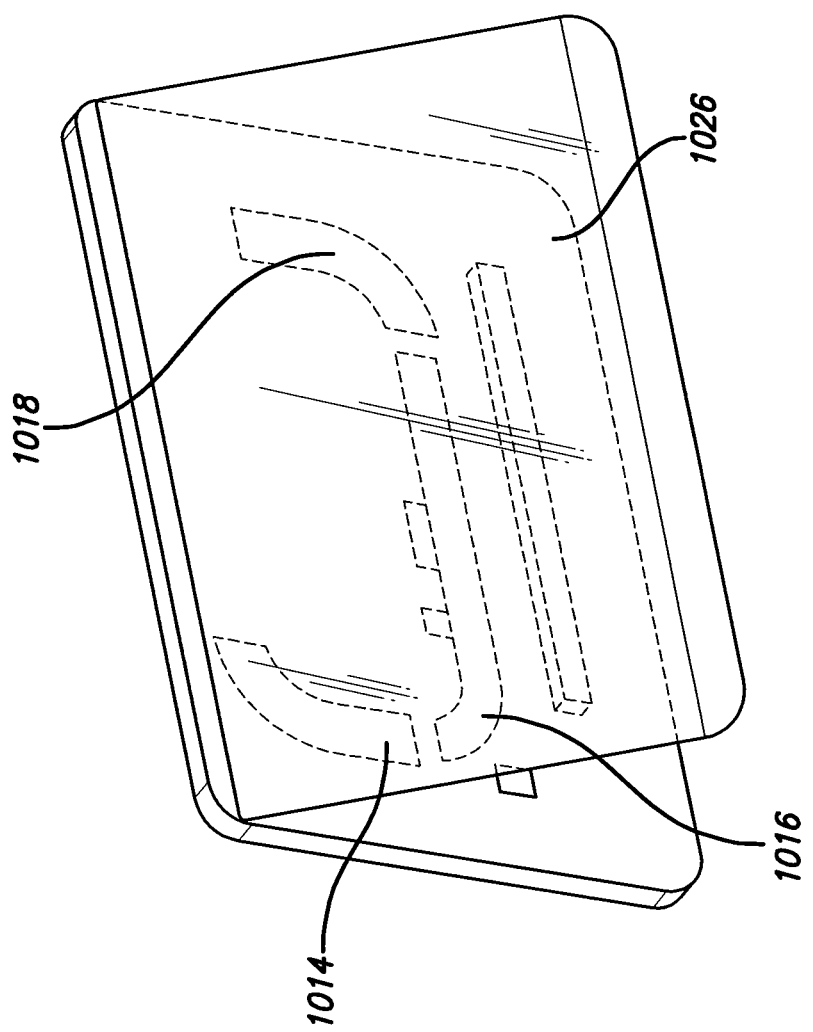
FIG. 11 is a reverse perspective view of the exothermal chemical PCR device of FIG. 10.

The LFS 1800 will detect labeled amplicons by making use of a sandwich capture technique with colloidal gold as the detector reagent (FIG. 11). The LFS will consist of a 20 nM or 40 nM colloidal gold-streptavidin conjugate 1810 dried down on a polyester conjugate pad 1802, a nitrocellulose matrix with an anti-DIG antibody applied in a uniform stripe 1804, a cotton absorbent pad 1806, and backing material (not shown). The PCR product 1700 will be applied to the conjugate pad portion of the LFS, and a running buffer will be added to wet the strip and ensure proper rehydration of the gold conjugate.

As the PCR product and buffer rehydrates and mixes with the conjugate, a complex will be formed where the colloidal gold-streptavidin 1810 binds to the labeled amplicon 1700 through biotin-streptavidin interaction. This mixture will then migrate up the LFS, at a rate to be determined by the strip characteristics. When the mixture reaches the test line, a strip of anti-digoxygenin antibody 1804, the colloidal gold-amplicon complex will bind to the line though interaction between the DIG-labeled nucleic acid 1700 and the antibody. A reddish color will form along this line as the complexes accumulate, and at a predetermined time (10-20 minutes) the strip will be visually read, with the presence of a reddish line indicating a positive result. Negative controls with combinations of no template DNA, irrelevant template DNA, nonlabeled primers, and without dUTP-DIG will be evaluated to ensure specificity. When no correctly labeled PCR product is present in the system, colloidal gold complexes will not form and no reddish test line will appear.

Figure 21:
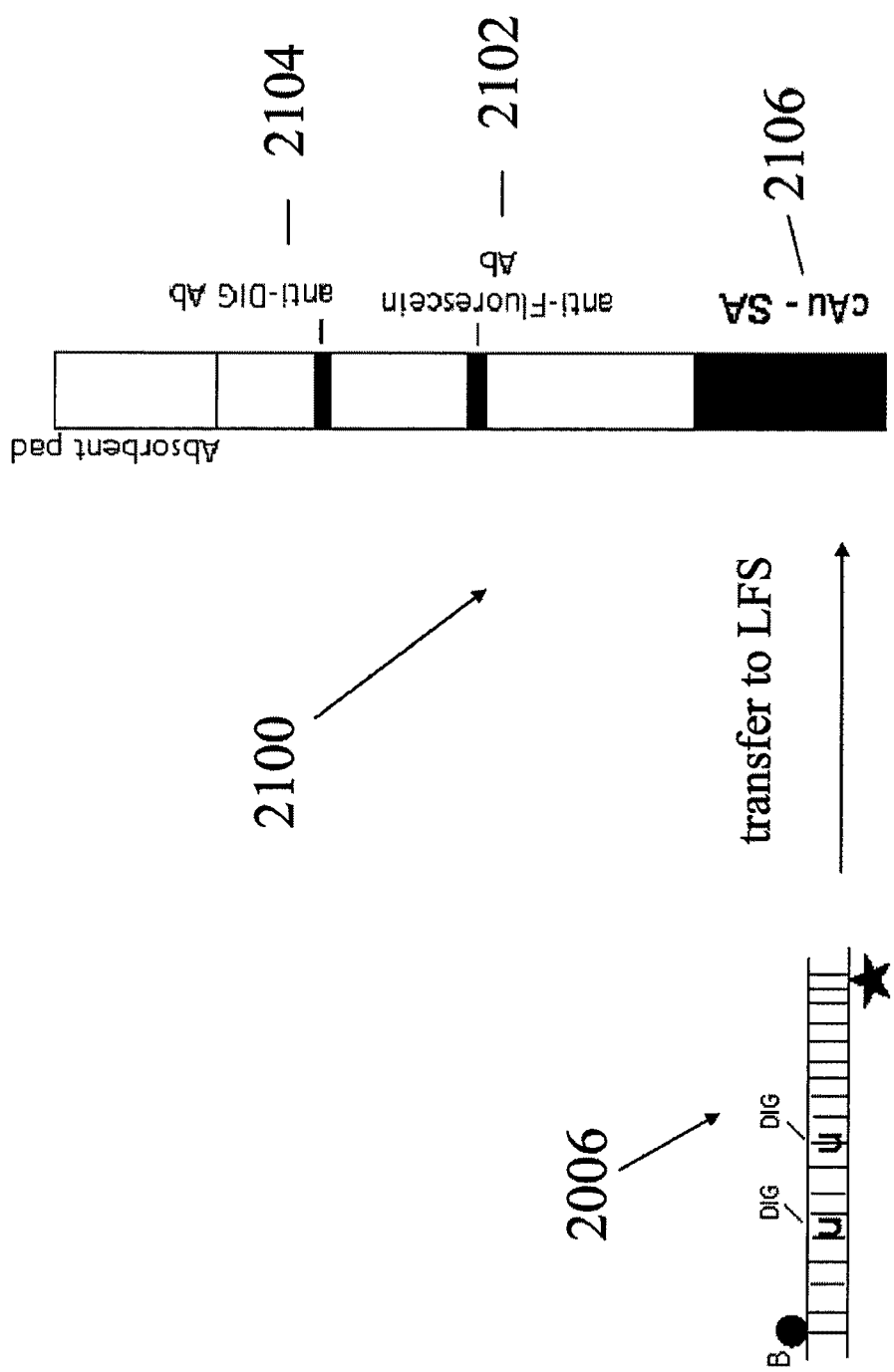
FIG. 21 is a schematic of the lateral flow strip used to detect the labeled DNA of FIG. 20.
Figure 22:
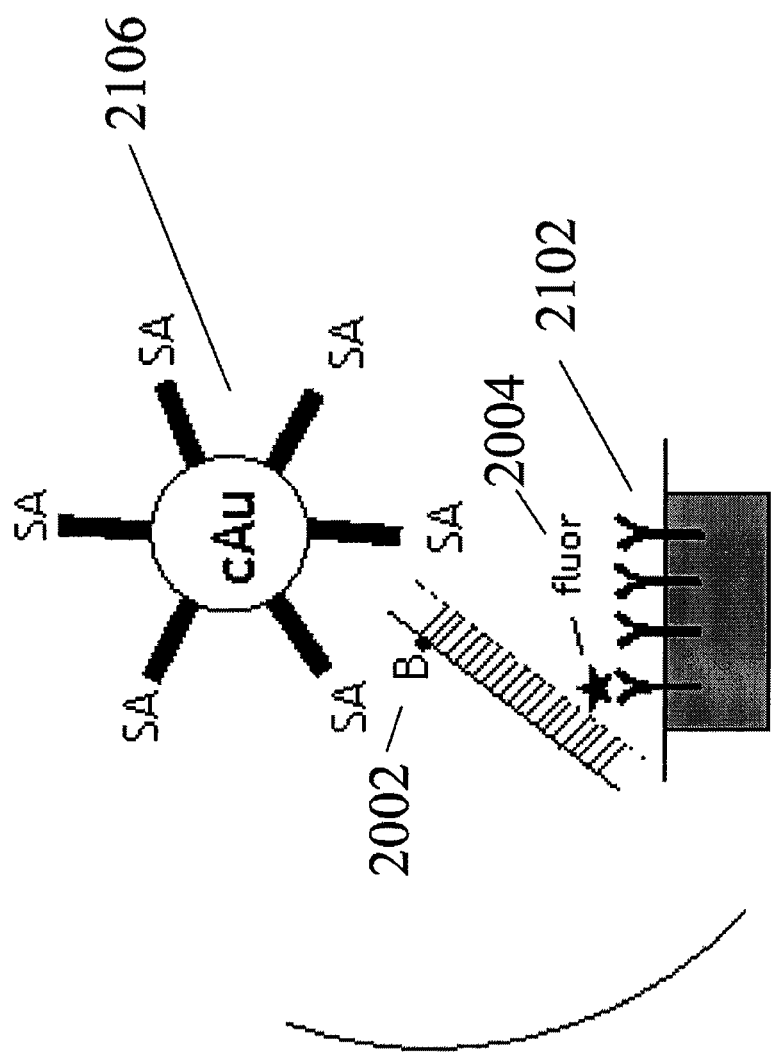
FIG. 22 is a schematic depicting the binding of the DNA on the lateral flow strip of FIG. 21.

There are two separate approaches which incorporate positive controls into the detection system. In the first approach, shown in FIGS. 20-22, quantified plasmid DNA that does not contain the test target sequence is included as an internal control in the test system described above. A portion of this internal control sequence will be amplified using specific primers. One primer will be prelabeled with biotin 2002, while the other primer will contain a fluorescein tag 2004. As the internal control nucleic acids 2006 are amplified, the biotin and fluorescent labels will be incorporated. Once the reaction is complete, the PCR product will be transferred to a LFS 1800 with two antibody stripes: an anti-fluorescein 2102 and an anti-Digoxygenin 2104. When this internal control amplicon mixes with the colloidal gold and moves up the LFS, it will be captured by the streptavidin gold conjugate 2106 though biotin-avidin binding, then by the anti-fluorescein antibody on the nitrocellulose. A reddish line will appear at 2102 as the colloidal gold-internal control complex accumulates. Since the PCR reaction mixture will contain dUTP-DIG 2008 for labeling the test amplicon, the dUTP-DIG will also be incorporated into the internal control amplicon. Because of this, the colloidal gold-internal control complex could potentially bind to the anti-DIG test line 2104 and produce false positive results. If this method is used, all of the colloidal gold-internal control complex would have to be captured by the anti-fluorescein antibody before the sample migrates to the anti-DIG antibody region. However, loading an excess of anti-fluorescein antibody onto the LFS could control for this.

A second approach, shown in FIGS. 23-25, still includes quantified control DNA 2300 in a single PCR reaction with the test system, as described in the first approach, but utilizes different primers and a second lateral flow strip 2400 for detection. In this method, both forward and reverse primers to amplify the internal control sequence are tagged with fluorescein 2302, and as PCR occurs, only fluorescein and dUTP-DIG 2104 are incorporated into the PCR product. To detect the internal control amplicon, the PCR product is split into two portions and run on two separate LFS. The test strip is the same as described above (see 2100), but the second strip 2400 contains an antifluorescein colloidal gold conjugate 2402 and an anti-DIG antibody line 2404. The anti-fluorescein colloidal gold conjugate captures the internal control amplicon, then the anti-DIG antibody captures this complex on the nitrocellulose to form a visible reddish line at 2404. The internal control amplicon will be present in the sample portion diverted to the test LFS, and vice versa, but neither should interfere with the detection strips as they cannot form sandwich complexes without both required tags for each system. While there may be some decrease in sensitivity using this approach due to the split sample, it is likely that with effective PCR amplification there will be an excess of amplicon to be detected.

Applications of Chemical Heating to Reverse Transcription

The above-described chemical temperature control methods (exothermic and/or endothermic reactions, ECPCMs, PCMs, insulators, geometry of the devices, etc.) are not limited to PCR applications. Chemical temperature control can be used in other diagnostic applications, for example with reverse transcription (RT). In one embodiment, a mixture of sodium acetate trihydrate and water is capable of generating sufficient heat to convert RNA to cDNA over a range of ambient temperatures. To demonstrate this capability, a 25% water/sodium acetate mixture was used. An eppendorf with an RT mixture was immersed in this heat mixture. The experiments were conducted at three ambient temperatures: 15° C., 22° C., and 30° C. in triplicate. The generated heat profiles are shown for the first 40 minutes in FIGS. 26 A-C (for the heat mixture at each temperature) and FIGS. 27 A-C (for the eppendorf with an RT mixture at each temperature).

Similar heat profiles (under the same three ambient temperatures) were conducted for heat mixtures comprising 0% and 15% water/sodium acetate mixtures. The heat profiles were conducted on a PCR heat block using high to low HIV-1 template copy numbers, and the efficiency of the RT was compared to that of the Biocentric one-step RT-PCR conditions for the same viral copy number templates. This is shown in FIG. 28 as a plot of the viral copies by Q-PCR vs. input HIV-1 equivalents copies/ml. This data shows that the temperature profiles are dependent on ambient temperature, but that the RT step is fairly tolerant to these temperature ranges. These combined data sets demonstrate that an exothermic mixture (for example sodium acetate trihydrate) can be used to provide sufficient energy to efficiently execute RT of viral pathogen RNA for diagnostics purposes at multiple ambient temperature conditions.

Besides PCR and RT, other diagnostics (biological, biochemical, or other) can use the products and methods described herein.

The foregoing description of the embodiments are presented for purposes of illustration and description. The description is not intended to be exhaustive or to limit the invention to the precise form disclosed, and obviously many modifications and variations are possible in light of the above teachings. While this invention has been particularly shown and described with reference to preferred embodiments thereof, it will be understood by those skilled in the relevant art(s) that various changes in form and details may be made therein without departing form the spirit and scope of the invention. For example, the use of chemical temperature controls is not limited to assays. Thus, the breadth and scope of the present invention should not be limited by any of the above-described exemplary embodiments, but should be defined only in accordance with the following claims and their equivalents.

What is claimed is:

1. An assay platform, comprising:
a reaction vessel for conducting a biochemical reaction under controlled temperature conditions;
a heating element thermally coupled to the reaction vessel, the heating element comprising:
an exothermic chemical reagent mixture; and
a phase change material disposed between the reaction vessel and the exothermic chemical reagent mixture,
wherein the amount of phase change material is configured to provide a controlled, substantially constant temperature to the reaction vessel for the biochemical reaction by being at least partially converted from its solid form to its liquid form when heated by an exothermic chemical reaction generated by the exothermic chemical reagent mixture, and
wherein said biochemical reaction is a nucleic acid amplification reaction.

2. The assay platform of claim 1, wherein said exothermic chemical reagent mixture comprises iron powder and carbon powder.

3. The assay platform of claim 1, wherein said exothermic chemical reagent mixture comprises a reduction of copper with magnesium.

4. The assay platform of claim 1, wherein said exothermic chemical reagent mixture comprises calcium oxide hydration.

5. The assay platform of claim 1, wherein said phase change material comprises a paraffin.

6. The assay platform of claim 1, wherein said phase change material is selected from the group consisting of a metal, an inorganic compound, an inorganic eutectic and an organic compound.

7. The assay platform of claim 1, wherein said nucleic acid amplification reaction is an isothermal nucleic acid amplification.

8. The assay platform of claim 1, wherein said reaction vessel comprises a biological organism requiring incubation at elevated, constant temperature.

9. The assay platform of claim 1, wherein said heating element has a well-defined working temperature.

10. The assay platform of claim 9, wherein said well-defined working temperature is between about 53 to about 70 degrees C.

11. The assay platform of claim 9, wherein said well-defined working temperature is between about 37 to about 55 degrees C.

12. The assay platform of claim 1, wherein said heating element has a well-defined working duration, after which the temperature of the heating element drops back to ambient levels.

13. The assay platform of claim 12, wherein said well-defined working duration is approximately one hour.

14. The assay platform of claim 1, further comprising a second heating element, wherein said second heating element has a different working temperature or duration, resulting in an assay platform having multiple heating plateaus.

15. The assay platform of claim 14, wherein said platform generates two heating plateaus.

16. The assay platform of claim 15, wherein said platform generates a first heating plateau comprising a working temperature between about 92 to about 96 degrees C. for approximately 5 minutes, followed by a second heating plateau comprising a working temperature between about 53 to about 70 degrees C. for approximately 80 minutes.

17. The assay platform of claim 15, further comprising a chemical cooling element.

18. The assay platform of claim 1, wherein the heating element is configured to maintain a constant temperature without using an electrical power source.

19. The assay platform of claim 1, wherein said exothermic chemical reagent mixture comprises magnesium.

20. An assay platform, comprising:
a reaction vessel for conducting a biochemical reaction under controlled temperature conditions;
a heating element thermally coupled to the reaction vessel, the heating element comprising:
an exothermic chemical reagent mixture; and
a phase change material disposed between the reaction vessel and the exothermic chemical reagent mixture,
wherein the amount of phase change material is configured to provide a controlled, substantially constant temperature to the reaction vessel for the biochemical reaction by being at least partially converted from its solid form to its liquid form when heated by an exothermic chemical reaction generated by the exothermic chemical reagent mixture, and
wherein said biochemical reaction is a reverse-transcription reaction.

21. An assay platform comprising:
a reaction vessel for conducting a biochemical reaction under controlled temperature conditions;
a heating element thermally coupled to the reaction vessel, the heating element comprising:
an exothermic chemical reagent mixture;
a phase change material disposed between the reaction vessel and the exothermic chemical reagent mixture; and
a density-driven closed-loop fluid circulation channel configured to achieve heat cycling in a circulation fluid as a function of the circulation fluid being heated as it passes through the heating element, and cooled when it is outside the heating element,
wherein the amount of phase change material is configured to provide a controlled, substantially constant temperature to the reaction vessel for the biochemical reaction by being at least partially converted from its solid form its liquid form when heated by an exothermic chemical reaction generated by the exothermic chemical reagent mixture.

22. The assay platform of claim 21, wherein said heating element acts as a heat source and an area outside of said heating element acts as a heat sink; wherein said heat source is at a lower elevation than said heat sink; and wherein said closed-loop fluid circulation channel has a minimally tortuous fluid path.

23. An assay platform, comprising:
a reaction vessel for conducting a biochemical reaction under controlled temperature conditions;
a heating element thermally coupled to the reaction vessel, the heating element comprising:
an exothermic chemical reagent mixture;
a phase change material disposed between the reaction vessel and the exothermic chemical reagent mixture; and
a wicking-driven linear channel configured to achieve heat cycling in a circulation fluid as a function of the circulation fluid being heated as it passes repeatedly over the heating element and being cooled when it is outside the heating element,
wherein the amount of phase change material is configured to provide a controlled, substantially constant temperature to the reaction vessel for the biochemical reaction by being at least partially converted from its solid form to its liquid form when heated by an exothermic chemical reaction generated by the exothermic chemical reagent mixture.

24. An assay platform, comprising:
a reaction vessel for conducting a biochemical reaction under controlled temperature conditions;
a heating element thermally coupled to the reaction vessel, the heating element comprising:
an exothermic chemical reagent mixture;
a phase change material disposed between the reaction vessel and the exothermic chemical reagent mixture; and
a spring-loaded, syringe-like pump driven linear channel configured to achieve heat cycling in a circulation fluid as a function of the circulation fluid being heated as it passes repeatedly over the heating element and being cooled when it is outside the heating element,
wherein the amount of phase change material is configured to provide a controlled, substantially constant temperature to the reaction vessel for the biochemical reaction by being at least partially converted from its solid form to its liquid form when heated by an exothermic chemical reaction generated the exothermic chemical reagent mixture.

* * * * *